US008461140B2

(12) United States Patent
Moriarty et al.

(10) Patent No.: US 8,461,140 B2
(45) Date of Patent: *Jun. 11, 2013

(54) SYNTHETIC BILE ACID COMPOSITIONS AND METHODS

(75) Inventors: Robert M. Moriarty, Michiana City, IN (US); Nathaniel E. David, Los Angeles, CA (US); Nadir Ahmeduddin Mahmood, Calabasas, CA (US)

(73) Assignee: Kythera Biopharmaceuticals, Inc., Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/486,955

(22) Filed: Jun. 1, 2012

(65) Prior Publication Data

US 2012/0238537 A1 Sep. 20, 2012

Related U.S. Application Data

(63) Continuation of application No. 12/541,045, filed on Aug. 13, 2009, now Pat. No. 8,242,294, which is a continuation-in-part of application No. 12/035,339, filed on Feb. 21, 2008.

(60) Provisional application No. 60/945,035, filed on Jun. 19, 2007, provisional application No. 60/956,875, filed on Aug. 20, 2007.

(51) Int. Cl.
*A61K 31/56* (2006.01)

(52) U.S. Cl.
USPC ........................................................ 514/182

(58) Field of Classification Search
USPC ........................................................ 514/182
See application file for complete search history.

(56) References Cited

U.S. PATENT DOCUMENTS

| | | | |
|---|---|---|---|
| 2,321,598 A | 6/1943 | Hoehn et al. | |
| 2,509,248 A | 5/1950 | Sarett | |
| 3,065,227 A | 11/1962 | Dodson | |
| 3,836,516 A | 9/1974 | Stempel et al. | |
| 4,322,553 A | 3/1982 | Chupp | |
| 4,917,827 A | 4/1990 | Batist et al. | |
| 5,827,853 A | 10/1998 | Blanc-Ferras et al. | |
| 6,114,336 A | 9/2000 | Blanc-Ferras et al. | |
| 6,313,128 B1 | 11/2001 | Blanc-Ferras et al. | |
| 6,653,492 B2 | 11/2003 | Faarup | |
| 6,936,402 B2 | 8/2005 | Kim et al. | |
| 7,902,387 B2 | 3/2011 | Prasad et al. | |
| 2005/0042539 A1 | 2/2005 | Kim et al. | |
| 2005/0261258 A1 | 11/2005 | Kolodney et al. | |
| 2005/0267080 A1 | 12/2005 | Kolodney et al. | |
| 2006/0127468 A1 | 6/2006 | Kolodney et al. | |
| 2006/0154906 A1 | 7/2006 | Kolodney et al. | |
| 2006/0222695 A1 | 10/2006 | Zadini et al. | |
| 2008/0318870 A1 | 12/2008 | Moriarty et al. | |
| 2008/0319221 A1 | 12/2008 | Junker et al. | |
| 2009/0270642 A1 | 10/2009 | Prasad et al. | |
| 2010/0130426 A1 | 5/2010 | Young et al. | |
| 2010/0145083 A1 | 6/2010 | Prasad et al. | |
| 2010/0160276 A1 | 6/2010 | Moriarty et al. | |
| 2011/0152552 A1 | 6/2011 | Prasad et al. | |
| 2011/0224448 A1 | 9/2011 | Prasad et al. | |

FOREIGN PATENT DOCUMENTS

| | | |
|---|---|---|
| FR | 2858413 A1 | 2/2005 |
| GB | 1 214 093 A | 12/1970 |
| JP | 10-120551 A1 | 5/1998 |
| WO | WO-93/03732 A1 | 3/1993 |
| WO | WO-94/27608 A1 | 12/1994 |
| WO | WO-98/05337 A1 | 2/1998 |
| WO | WO-02/088166 A1 | 11/2002 |
| WO | WO-2005/112942 | 12/2005 |
| WO | WO-2005/117900 A1 | 12/2005 |
| WO | WO-2006/133160 A2 | 12/2006 |
| WO | WO-2008/157635 A2 | 12/2008 |

OTHER PUBLICATIONS

"Deoxycholic Acid". New Zealnd Pharamceuticals Ltd., (2007) http://www.nzp.co.nz/products.php?cid=2&pid=2.

Arnone et al., "Perfluoro-cis-2,3-Dialkyloxaziridines: Effective Reagents for the Selective Oxidation of Ethers to Carbonyl Compounds." Journal of Organic Chemistry, 1995, vol. 60(8), pp. 2314-2315.

Babcock, J.C. et al., "Reduction Methylation of Steroid Ketones", Nov. 5, 1952, vol. 74, pp. 5472-5474.

Barton, D.H.R., et al. "A practical catalytic method for the preparation of steroidal 1,4-dien-3-ones by oxygen atom transfer from iodoxybenzene to diphenyl diselenide", J. Chem. Soc., Perkin Transactions 1: Organic and Bio-Organic Chemistry (1972-1999) (1982), (8), 1947-1952.

Batcho et al. "C-20 Stereospecific Introduction of a Steroid Side Chain." Journal of the American Chemical Society, 1981, vol. 103(5), pp. 1293-1295.

Bell, A.M. et al., "Microbiological hydroxylation. Part XVIII. Introduction of 16-, 9-, and 3-hydroxy-groups into dioxygenated 5-androstanes by the fungus *Diaporthe celastrina*", J. Chem. Soc., Perkin Transactions 1: Organic and Bio-Organic Chemistry (1972-1999) (1975), (14), 1364-1366.

Caspi, E. "Degradation of Corticosteroids. III.1,2 Catalytic Hydrogenation of Cortisol", J. Org. Chem., 1959, 24, 669-673.

Chambers, V.E.M. et al., "Microbiological Hydroxylation. Part XIV.1 Hydroxylation in the Terminal Rings of Dioxygenated 5a-Androstanes with the Fungi *Wojnowicia graminis* and *Ophiobolus herpotrichus*", J.C.S. Perkin I, Jun. 27, 1974, 4/1285, pp. 55-58.

Chang et al. "Seroflocculating Steroids" Clin. Chem. (1964), 10(1), 83-91.

(Continued)

*Primary Examiner* — Barbara P Badio
(74) *Attorney, Agent, or Firm* — Foley & Lardner LLP

(57) ABSTRACT

Bile acids and related compositions and methods of synthesis and use. More specifically, deoxycholic acid and related compositions, said compositions being free of all moieties of animal origin and free of pyrogenic moieties.

6 Claims, 1 Drawing Sheet

OTHER PUBLICATIONS

Chang et al. "Seroflocculating Steroids. II. General." Contribution from the Division of Chemistry and Division of Pathology and Microbiology, Medical Units, University of Tennessee. (1957) 79:2161-2163.

Child et al., "Preparation and mass spectral behavior of some 5β-cholenoic acids." Canadian Journal of Biochemistry, 1979, vol. 57(3), pp. 216-225.

Constantin et al.: "Introduction of the 11-keto function in the steroids" J. Am. Chem. Soc., vol. 74, No. 15, 1952, pp. 3908-3910, XP002509787.

Danielsson et al. "On the Composition of the Bile Acid Fraction of Rabbit Feces and the Isolation of a New Bile Acid: 3a, 12a-Dihydroxy-5a-cholanic Acid". The Journal of Biological Chemistry, (1963) 238 (12): 3846-3852.

Dias et al., "13C nuclear magnetic resonance data of bile acid derivatives." Spectrochimica Acta, Part A: Molecular and Biomolecular Spectroscopy, 2000, vol. 56A(1), pp. 53-77.

Dobriner, K., et al. "The Isolation of ?9-Etiocholenol-3(a)-One-17 From Human Urine", Journal of Biological Chemistry (1947), 169, 221-222.

Dodson et al. "Microbiological Transformations. VII. The Hydroxylation of Steroids at C-9". Contribution from the Biological and Chemical Search Divisions of G. D. Searle and Co., Chicago 80, Ill., (1961) vol. 83: 4631-4635.

Dosen, "The Biochemist's Handbook," MIR publishers, 1991, p. 173.

Fieser, L.F. et al., "Oxidation of Steriods. IV. Methyl ?9(11)-Lithocholenate and Methyl 9a,11a-Oxidolithocholanate1,2", Jan. 1951, vol. 73, pp. 118-122.

Fukushima, D. et al. "The Characterization of Four New Metabolites of Adrenocortical Hormones", Journal of Biological Chemistry (1955), 212, 449-460.

Gallo-Torres et al., "Some effects of deoxycholate administration on the metabolism of cholesterol in man." The American Journal of Clinical Nutrition, vol. 32, pp. 1363-1375, 1979.

Herzog et al., "11-Oxygenated Steroids. II. The reduction of 11-carbonyl to 11-aplha-hydroxyl in the etiocholane series", J. Am. Chem. Soc., T. 75, No. 2, 1953, 269-272, XP002509785.

Heymann, H. et al., "A New Route to 11-Ketosteroids by Fission of a ?9(11)—Ethylene Oxide1,2", Nov. 1951, vol. 73, pp. 5252-5265.

Hofmann et al. "A proposed nomenclature for bile acids". J. Lipid Res. (1992) 33: 599-604.

Hofmann. "Bile Acids: The good, the Bad, and the Ugly". News Physiol. Sci. (1999) 14: 24-29.

Iida, T. et al., "A facile one-step synthesis of ?1-4-3-keto bile acid esters by iodoxybenzene and benzeneselenic anhydride," Journal of Lipid Research, 29(8), 1988, 1097-1101.

International Search Report and Written Opinion for PCT/US2010/045385, dated Jun. 7, 2011.

Iuliano et al., "Synthesis of deoxycholic-derived chiral stationary phases possessing both arylcarbamate and arylamide moieties: evaluation of their chiral discrimination properties in the HPLC resolution of racemic compounds." Tetrahedron: Asymmetry, 2001, vol. 12(20), pp. 2811-2825.

Jones, R.N., et al. "Studies in Steroid Metabolism. IV. The Characterization of Carbonyl and Other Functional Groups in Steroids by Infrared Spectrometry", J. Am. Chem. Soc. (1948), 70, 2024-2034.

Kakushima, "Total synthesis of (±)-5β,8a-androst-9(11)-ene-3,17-dione," Canadian Journal of Chemistry, 1979, vol. 57(24), pp. 3354-3356.

Kametani et al. "First Total Synthesis of (+)-Chenodeoxycholic Acid". J. Am. Chem. Soc.. (1981) 103: 2890-2891.

Kasal. "Hydrogenation of 12-oxo-5β-chol-9(11)-enates on Platinum" Collection of Czechoslovak Chemical Communications (1981), 46(8), 1839-49.

Katona et al. "Synthesis, Characterization, and Receptor Interaction Profiles of Enantiomeric Bile Acids". J. Med. Chem., (2007) 50, 6048-6058.

Katona, et al. "Enantiomeric Deoxycholic Acid: Total Synthesis, Characterization, and Preliminary Toxicity toward Colon Cancer Cell Lines". J. Org. Chem., (2007) 72, 9298-9307.

Kolonin et al. "Reversal of obesity by targeted ablation of adipose tissue" Nature Medicine, Nature Publishing Group, (2004) 10(6): 625-632.

Kyd, P., et al. "Experimental oleic acid-induced cholelithiasis in the rabbit associated with increased biliary 5-deoxycholic acid", Biochemical Journal (1972), 128(1), 169-172.

Lieberman, S. et al., "Studies in Steroid Metabolism II. Identification and Characterization of Ketosteroids Isolated from Urine of Healthy and Diseased Persons," The Journal of Biological Chemistry 1948, 172, 263-295.

Maneerat et al. "Bile acids are new products of a marine bacterium, *Myroides* sp. Strain SM1". Appl. Microbiol. Biotechnol., (2005) 67: 679-683.

Marker et al. "Sterols. LXIX. Oxidation Products of Sarsasapogenin. Sarsasapogenoic Acid and Related Substances". J. Am. Chem. Soc., (1939) 61(8): p. 2072-2077.

Matsuoka et al. "Micelle formation of sodium deoxycholate and sodium ursodeoxycholate (Part 1)". Biochem. Biophys. Acta. 1580, (2002) pp. 189-199.

Mazur et al. "The Synthesis of the Steroidal Sepogenins". J. Am. Chem. Soc., (1960) 82, 5889-5908.

Micheli, et al. "Total Syntheses of Optically Active 19-Norsteroids. (+)-Estr-4-ene-3,17-dione and (+)-13β-Ethylgon-4-ene-3,17-dione". J. Org. Chem., (1975) vol. 40, No. 6, pp. 675-681.

Mickova et al., "Reduction of 12-oxo Derivatives of Some Bile Acids." Collection of Czechoslovak Chemical Communications, 1985, vol. 50(5), pp. 1239-1243.

Mukawa, K. et al., "Studies on the Transformation of Unnatural Steroids by Micro-organisms. 14-βHydroxylation of Androstane Derivative," Journal of the Chemical Society: Chemical Communications, 1971, vol. 18, pp. 1060-1061.

Mukhopadhyay et al., "Chemistry and biology of bile acids". Current Science, (2004) 87(12) 1666-1683.

Norton et al.: "Crysta1 data (I) for some bile acid derivatives" Acta Cryst., vol. 19, 1965, pp. 477-478, P002509788.

Osawa "Dehydration of Bile Acids and Their Derivatives. X. A Study of the Physical Properties of Various 3a-Hydroxycholenates and Their Derivatives, With Special Reference to Their Optical Rotatory Dispersions" Bulletin of the Chemical Society of Japan (1962), 35(3), 381-7.

Peron, F.G., et al. "Steroids of Guinea Pig Urine", Journal of Biological Chemistry (1956), 223, 877-883.

Potluri, V.K. et al., "Bile Acid-Derived Molecular Tweezers: Study of Solvent Effects in Binding, and Determination of Thermodynamic Parameters by an Extraction-Based Protocol," J. Org. Chem., 2000, 65, 7764-7769.

Reichstein et al. "Über Gallensäuren und verwandte Stoffe. 12. Mitteilung. Vereinfachte präparative Herstellung reiner Desoxycholsäure und eigener ihrer Derivate" Helvetica Chimica Acta, vol. 25, No. 5, Oct. 24, 2004, pp. 797-805, XP002509789.

Ridlon et al. "Bile salt biotransformations by human intestinal bacteria". J. Lipid Res., (2006) 47(2): p. 241-259.

Roda et al. "Quantitative aspects of the interaction of bile acids with human serum albumin". J. Lipid Res. (1982) 23(3): p. 490-495.

Rotunda et al. "Detergent effects of sodium deoxycholate are a major feature of an injectable phosphatidylcholine formulation used for localized fat dissolution". Dermatol. Surgery, (2004) 30(7) :1001-1008.

Rotunda et al. "Lipomas treated with subcutaneous deoxycholate injections". J. Am. Acad. Dermatol., (2005) pp. 973-978.

Rotunda et al. "Mesotherapy and Phosphatidylcholine Injections: Historical Clarification and Review" Dermatologic Surgery, (2006) 32: 465-480.

Sarett, L.H. et al., "Partial Synthesis of Etiocholene-9-OL-3(a)-one-17", The Journal of Biological Chemistry, ASSBMB, www.jbc.org, Dec. 5, 1947, pp. 185-187.

Scott et al. "A Symmetry Rule for Chiral Olefins" Tetrahedron (1970), 26(15), 3695-3715.

Seebeck et al. "Über Gallensäuren und verwandte Stoffe. 21. Mitteilung. 3-Alpha-acetoxy-12-keto-cholen-(9)-säure und 3-Alpha-oxy-cholen-(9)-säure" Helvetica Chimica Acta, vol. 26, No. 2, Oct. 24, 2004, pp. 536-562, XP002509786.

Shirasaka, M., et al. "The microbial reduction of [Delta]4-3-ketone pregnene compounds by a fungus, *Alternaria bataticola*", Biochemistry and Biophysics (1959), 85, 277-280.

Shoppe, von C.W. et al., "98. Androsten-(9)-dion-(3,17), Bemerkungen zu H.Reich und A. Lardon1), Androsten-(9)-ol-(3β)-on-(17)", vol. xxx, Fasciculus III (1947), pp. 766-768.

Shoppee. "252. The Structure of Adreno-cortical Metabolites: ?9:11-Androstene-3 : 17-dione." J. Chem. Soc., 1946, 1134-1137.

Stefanovic, M., et al. "An improved preparation of 3-[alpha]-acetoxy-11,20-diketo-(5[beta])-pregnane, the key intermediate in the synthesis of 11-oxygenated corticosteroids", Tetrahedron Letters (1967), (48), 4799-4803.

Svensson et al. "The Design and Bioactivation of Presystemically Stable Prodrugs". Drug Metabolism Reviews, (1988) 19(2): 165-194.

Szczebara et al. "Total biosynthesis of hydrocortisone from a simple carbon source in yeast". Nature Publishing Group, (2003) vol. 21:143-149.

Szczepanik et al., "Characterization of bile acid methyl ester acetate derivatives using gas-liquid chromatography, electron impact, and chemical ionization mass spectrometry." Journal of Lipid Research, 1976, vol. 17(4), pp. 314-334.

Talmage et al. "Quingestrone—Determination of Minute Quantities of Decomposition Products by Paper Chromatography" Journal of Pharmaceutical Sciences (1964), 53(1), 76-9.

Woodward et. al. "The Total Synthesis of Steroids". J. Am. Chem. Soc., (1952) 74(17) : 4223-4251.

Yoshizawa et al., "Isolation and Structural Elucidation of the Degradation Products of Pregnanediol Disulfate obtained by Hot Acid Hydrolysis (Clinical Analysis on Steroids. XXII))." Chemical & Pharmaceutical Bulletin, 1982, vol. 30(7), pp. 2474-2486.

Ziegler et al., "The AlCl3-LiAlH4 reduction of ?9(11)-12-oxo and ?9(11)-12-hydroxy steroids." Canadian Journal of Chemistry, 1968, vol. 46(9), pp. 1574-1577.

International Search Report and Written Opinion for PCT/US2008/067391, dated Jan. 13, 2009.

International Search Report and Written Opinion for PCT/US2010/045385, dated Apr. 24, 2012.

Kiprianov, G. I.; Volovel'skii, L. N. Zhurnal Obshchei Khimii (1964), 34(1), 336-8. Translation provided.

Lieberman et al.: "Studies in steroid metabolism" J. Biol. Chem., vol. 196, No. 2, 1952, pp. 793-805.

Kagan et al. "No. 118.—Preparation et Proprieties de Quelques Dioxolanes Derives d'Acides Biliaires" Bulletin de la Societe Chimique de France (1957), 699-704.

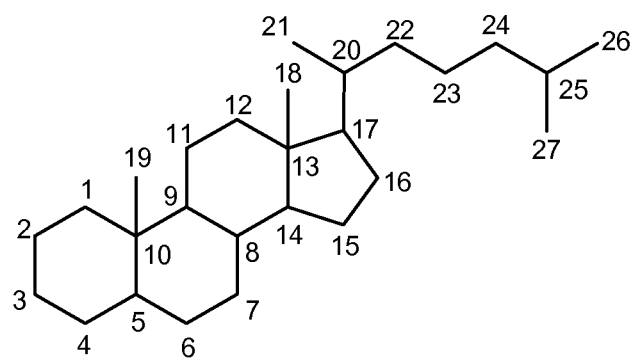

SYNTHETIC BILE ACID COMPOSITIONS AND METHODS

CROSS-REFERENCE TO RELATED APPLICATIONS

This application is a continuation application and claims benefit under 35 U.S.C. §120 of U.S. application Ser. No. 12/541,045, filed Aug. 13, 2009, which is now U.S. Pat. No. 8,242,294, and which is a continuation in part and claims benefit under 35 U.S.C. §120 of U.S. application Ser. No. 12/035,339 filed Feb. 21, 2008, which in turn claims the benefit under 35U.S.C. 119(e) to provisional applications U.S. application Ser. No. 60/945,035 filed on Jun. 19, 2007 and U.S. application No. 60/956,875 filed on Aug. 20, 2007. The contents of each of the prior applications are incorporated herein by reference in their entirety.

FIELD OF THE INVENTION

The present invention relates broadly to bile acids and related compositions and methods. In one aspect, the present invention relates to deoxycholic acid and related compositions, useful intermediates, and methods for synthesis thereof. In another aspect, the present invention relates to use of the present compositions and methods as pharmaceutical compositions as well as methods for the manufacture thereof. Importantly, the bile acids of the present invention are not isolated from mammalian and microbial organisms naturally producing these acids and thus are free of any toxins and contaminants associated with such organisms.

BACKGROUND OF THE INVENTION

Cholanology, the study of bile acids, and particularly bile acid chemistry has been of interest for the better part of a century. Although much is known, bile acid chemistry involves a wide variety of chemical entities, many with surprising properties. For a review, see, e.g., Mukhopadhyay, S, and U. Maitra., Current Science 87: 1666-1683 (2004) ("Chemistry and biology of bile acids"), incorporated herein by reference.

Bile acids are characterized by two connecting units, a rigid steroid nucleus and a short aliphatic side chain (see FIG. 1 of the present application). See, Hofmann, A. F., et al. For a proposed nomenclature for bile acids, see J. Lipid Res. 33:599-604 (1992). Both the nucleus and the side chain have a large number of possible steric arrangements. The nucleus can be altered by expansion or contraction of individual rings, and the side chain can be shortened or lengthened. In addition, both parts of the bile acid molecule have a large number of possible polar substituents. Ionizing groups may be present on the nucleus or the side chain. Finally, conjugating groups may be present on the nucleus (e.g., sulfate, glucuronate, phosphate) or on the side chain (glycine or taurine or other amino acids, or even sugars). The side chain structure determines the class of the compound (bile acids or bile salts).

Bile acids are amphiphiles, having both an amphiphilic and amphipathic "face"

By convention, the hydrophobic surface is called the "β-face" and the hydrophilic surface is called the "α-face". The β-face is lipid soluble and the α-face is relatively polar, in general. There are bile acids, such as those having polar groups (hydroxyl groups, in naturally occurring bile acids) on the hydrophobic face as well as on the hydrophilic face, e.g., ursodeoxycholic acid. The amphipathic nature of the molecule is responsible for its forming mixed micelles with amphipathic but water-insoluble lipids, such as phosphatidylcholine. Bile acids will not solubilize dietary lipids in the form of mixed micelles unless bile acids are above a critical concentration, termed the critical micellization concentration.

The bile acids found in greatest proportion in humans are chenodeoxycholic acid and deoxycholic acid. Deoxycholic acid is also known as deoxycholate, cholanoic acid, and 3α,12α-dihydroxy-5β-cholanate. In the human body deoxycholic acid is used in the emulsification of fats for the absorption in the intestine. In research, deoxycholic acid is used as a mild detergent for the isolation of membrane associated proteins. When substantially pure, deoxycholic acid is a white to off-white crystalline powder form. Deoxycholic acid is one of the four main acids produced by the liver. It is soluble in alcohol and acetic acid. The CAS number for deoxycholic acid is [83-44-3].

Rapid removal of body fat is an age-old ideal, and many substances have been claimed to accomplish such results, although few have shown results. "Mesotherapy", or the use of injectables for the removal of fat, is not widely accepted among medical practitioners due to safety and efficacy concerns, although homeopathic and cosmetic claims have been made since the 1950's. Mesotherapy was originally conceived in Europe as a method of utilizing cutaneous injections containing a mixture of compounds for the treatment of local medical and cosmetic conditions. Although mesotherapy was traditionally employed for pain relief, its cosmetic applications, particularly fat and cellulite removal, have recently received attention in the United States. One such reported treatment for localized fat reduction, which was popularized in Brazil and uses injections of phosphatidylcholine, has been erroneously considered synonymous with mesotherapy. Despite its attraction as a purported "fat-dissolving" injection, the safety and efficacy of these cosmetic treatments remain ambiguous to most patients and physicians. See, Rotunda, A. M. and M. Kolodney, Dermatologic Surgery 32: 465-480 (2006) ("Mesotherapy and Phosphatidylcholine Injections: Historical Clarification and Review").

WO 2006/133160 (incorporated herein by reference in its entirety including figures) describes methods for lipomodeling, e.g., reduction of a fat depot, by administering a neuropeptide Y receptor antagonist to the site of the fat depot. Kolonin M. G. et al., Nat. Med. June 10(6):625-32 (2004), describes fat selective pro-apoptotic peptides having potent fat cell killing effects. The described pro-apoptotic peptides require access to the vasculature to kill.

Recently published literature reports that deoxycholic acid has fat removing properties when injected into fatty deposits in vivo. See, WO 2005/117900 and WO 2005/112942, as well as US2005/0261258; US2005/0267080; US2006/127468; and US20060154906, all incorporated herein by reference in their entirety including figures). Deoxycholate injected into fat tissue has two effects: 1) it kills fat cells via a cytolytic mechanism; and 2) it causes skin tightening. Both of these effects are required to mediate the desired aesthetic corrections (i.e., body contouring). Because deoxycholate injected into fat is rapidly inactivated by exposure to protein and then rapidly returns to the intestinal contents, its effects are spatially contained. As a result of this attenuation effect that confers clinical safety, fat removal therapies typically require 4-6 sessions. This localized fat removal without the need for surgery is beneficial not only for therapeutic treatment relating to pathological localized fat deposits (e.g., dyslipidemias incident to medical intervention in the treatment of HIV), but also for cosmetic fat removal without the attendant risk inherent in surgery (e.g., liposuction). See, Rotunda et al., Dermatol. Surgery 30: 1001-1008 (2004) ("Detergent effects of sodium deoxycholate are a major feature of an injectable phosphatidylcholine formulation used for localized fat dissolution") and Rotunda et al., J. Am. Acad. Dermatol. (2005: 973-978) ("Lipomas treated with subcutaneous deoxycholate injections"), both incorporated herein by reference.

Pharmaceutical grade bile acid preparations are commercially available at relatively low cost. This low cost is due to the fact that the bile acids are obtained from animal carcasses, particularly large animals such as cows and sheep. Importantly, as with all medicaments from animal sources, there is concern that the animal-derived bile acid products may contain animal pathogens and other harmful agents such as animal or microbial metabolites and toxins, including bacterial toxins such as pyrogens.

Such animal pathogens can include prions, which are thought to be a type of infectious pathogenic protein that may cause prion diseases. Prion diseases are degenerative disorders of the nervous system. One such disease, "Mad cow" disease (thought to be a variant of Creutzfeldt-Jakob disease (CJD)), is thought to be caused by a prion present in edible beef from diseased cows. Most cases are sporadic with unknown mode of transmission; some cases are inherited; and a small number have been transmitted by medical procedures. The spread of human prion diseases through consumption of infected material has been implicated historically in kuru and recently in variant CJD. Other animal prion diseases (scrapie of sheep, transmissible mink encephalopathy, chronic wasting disease of cervids, and bovine spongiform encephalopathy) all seem to be laterally transmitted by contact with infected animals or by consumption of infected feed. Risk assessment and predictions of future events pertaining to prion diseases are difficult to ascertain because of the different modes of transmission, the unpredictable species barriers, the variable distribution of infectivity in tissues, and strain variations found in some diseases.

In general, animal products may be exposed to microbial organisms which produce pyrogens (fever-causing substances). Bacterial contaminants of food and/or pharmaceutical products are also a serious issue as evidenced by contamination of food stuffs by enterohemoragic *E. coli*. Products such as meats derived from cows as well as produce such as apples, spinach, and the like, have been implicated in such contamination. In such cases, it is the toxin produced by the bacteria (rather than the bacteria itself) that produces adverse effects in humans. Such adverse effects include severe diarrhea, kidney failure and in the extreme situations, death. Bacterial endotoxins, a type of pyrogen, must be substantially excluded from all pharmaceutical compositions.

Animal products are generally purified by a process of elimination, i.e., rather than selecting the end-product from a mix, the end product is the material remaining after exclusion of impurities. And, in addition to the potential animal moieties such as pathogens, another artifact of purification from animal sources is that the end-product is a mixture of one or more bile acids. For example, commercial preparations of deoxycholic acid contain some chenodoxycholic acid, as well as cholic acid, which is a precursor to both deoxycholic acid and chenodeoxycholic acid in mammalian bile acid synthesis. Because the exact proportion of deoxy/cheno/cholic is not preselected, this may result in lot-to-lot variation when contemplating manufacturing large amounts of bile acids. Such lot-to-lot variation can be problematic and may engender additional steps in garnering regulatory approvals or quality control, particularly in efforts to produce a pharmaceutical composition. Clearly, producers would desire lot-to-lot predictability in manufacturing bile acid pharmaceutical compositions.

Currently, the concerns regarding animal-derived products containing animal pathogens and other harmful agents has been addressed by sourcing from isolated and inspected animals. For example, deoxycholic acid from animals in New Zealand are a source of bile acids for human use under US regulatory regimes, as long as the animals continue to remain isolated and otherwise free of observable pathogens.

Implicitly, by the need for such governmentally controlled regulatory regime is the recognition of an intrinsic risk of transmission of animal pathogens when animal-derived medicaments are injected. Where non-animal medicament alternatives become available, the governmental regulatory regime is no longer needed. An example of such alternative (non-animal medicament replacing animal-derived medicament) and associated advantages is insulin for human use. The manufacture of beef insulin in the United States was discontinued in 1998, and pork insulin for human use was discontinued in January of 2006. Although animal insulin can be obtained from herds not known to have had exposure to BSE-causing or other pathogenic agents, the manufacturing facilities or processes can expose the animal ingredients to animals which have had exposure to the pathogens. The risk of transmission of pathogenic agents to humans can be eliminated with the use of insulin that is manufactured recombinantly or synthetically. For consumers, the insulin situation is instructive: where synthetic material is freely available, the risk of transmission of animal pathogens is in theory eliminated. For producers, the ability to produce a pure chemical entity that is substantially free of material of animal pathogens is advantageous for safety, quality, and regulatory purposes. Further, a synthetic process typically provides for a more reproducible product than that derived from biological sources.

Presently, because of the relative abundance of animal carcass-derived bile acids, the industry has not taken steps to either fully chemically synthesize bile acids, or prepare bile acids using phytosterol or microbial starting materials. And although bile acid derivatives have been synthesized, this work again primarily involved animal-derived bile acids as starting materials for steroid chemistry, due to the low cost and ready availability of animal materials. Despite historically active efforts in phytosterol research, there are no readily-commercially available phytosterol-derived bile acid pharmaceutical grade compositions. See, e.g., Mukhopadhyay, S, and U. Maitra., Current Science 87: 1666-1683, 1670 (2004) (Noting that the total synthesis of any bile acid had not been performed subject to a 1981 reference, Kametani et al. J. Am. Chem. Soc. 103: 2890 (1981) ("First Total Synthesis of (+)-Chenodeoxycholic Acid"). Microbial, such as bacterially-produced bile acids, have been used in situ as bacterial products, e.g., for marine oil spill clean-up. See, Maneerat et al., Appl. Microbiol. Biotechnol. 76: 679-683 (2004) ("Bile acids are new products of a mariene bacterium, *Myroides* sp. Strain SM1").

In order to realize the full potential of deoxycholic acid for the removal of fat, it is imperative that the concerns over the use of animal derived products be further addressed. Clearly, there is a need for suitable quantities of efficacious bile acids and related compositions, such as the deoxycholic acids, that are known from the outset to be free from moieties of animal origin (or pathogenic moieties capable of acting in an animal, particularly a mammal, and for human use, having a deleterious effect on a human), and other harmful agents such as animal or microbial metabolites, toxins, including bacterial toxins, such as pyrogens, for use as medicaments in humans. The present invention addresses this concern by providing synthetically prepared bile acid compositions free of the potential risk of animal pathogens and other harmful agents. The disclosed bile acid compositions can be used in adipolytic therapy and will serve to further advance research and developmental efforts in the area of localized fat removal.

SUMMARY OF THE INVENTION

Adequate quantities of suitable bile acid as a defined pharmaceutical composition is herein provided, as well as methods for synthesis thereof. Bile acid compositions and methods so provided are not isolated from mammalian or microbial organisms that naturally produce the bile acids. In one aspect, particular deoxycholic acid pharmaceutical compositions which are free of all moieties of animal origin and of mammalian and/or bacterial pyrogens, and related methods for production and use are provided. In another aspect, adequate quantities of suitable deoxycholic acids as defined pharmaceutical compositions are provided which can be used as an injectable pharmaceutical composition for localized fat removal, along with related compositions, methods for manufacture and methods of use. The defined deoxycholate injectates of the present invention may be combined with a molecule that causes fat to die by an orthogonal mechanism, e.g., NPY antagonists and/or fat selective pro-apoptotic peptides, to provide agents to be used to create a more potent means to mediate body contouring in fewer therapeutic sessions.

BRIEF DESCRIPTION OF THE DRAWINGS

FIG. 1 is a drawing representing the structure of bile acids, including the numbering system for the carbons of the bile acid skeleton.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used herein, certain terms have the following defined meanings.

The term "pathogen" refers to a specific causative agent of a disease.

The term "animal origin" refers to originating from any of a kingdom (Animalia) of living things including many-celled organisms and single celled organisms.

The term "mammalian origin" refers to originating from any mammalian organism. The term "mammalian organism" refers to a class (Mammalia) of warm-blooded higher vertebrates (as placentals, marsupials, or monotremes) that nourish their young with milk secreted by mammary glands, have the skin usually more or less covered with hair, and include humans.

The term "microbial origin" refers to originating from any microbial organism. The term "microbial organism" refers to a domain (Bacteria) of prokaryotic round, spiral, or rod-shaped single-celled microorganisms that may lack cell walls or are gram-positive or gram-negative if they have cell walls, that are often aggregated into colonies or motile by means of flagella, that typically live in soil, water, organic matter, or the bodies of plants and animals, that are usually autotrophic, saprophytic, or parasitic in nutrition, and that are noted for their biochemical effects and pathogenicity.

The term "lower alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—).

The term "ethane dithiol or dithiane precursor" refers to a reagent that, with reaction with a carbonyl group, will form an ethane dithiol or dithiane group.

The term "oxidizing agent" refers to a reagent which can accept electrons in an oxidation-reduction reaction. In this way, halogen or oxygen can be added to a molecule or hydrogen can be removed from a molecule.

The term "desulfurization reagent" refers to a reagent which can react with a sulfide. In one aspect, a desulfurization reagent can react with a sulfide containing molecule to remove the sulfide group from the molecule.

The term "reducing agent" refers to a reagent which can donate electrons in an oxidation-reduction reaction. In this way, halogen or oxygen can be removed from a molecule or hydrogen can be added to a molecule.

The term "electrophilic acetyl group" refers to an acetyl group as an electrophile, a group which is attracted to electrons and tends to accept electrons.

The term "acetylating reagent" refers to a reagent in which can add an acetyl group to a molecule.

The term "acid" refers to a proton donor.

The term "hydrogenation reagent" refers to a reagent that can donate hydrogen to a molecule.

The term "dehydration reagent" refers to a reagent that can react with water. In one aspect, a dehydration reagent can react with water that is removed from a molecule.

In various aspects described herein, the present invention provides compositions (and useful intermediates) for pharmaceutical use, methods of synthesis thereof, and methods of use of the present pharmaceutical compositions.

Importantly, the present bile acid compositions are free of risks inherent in material obtained from animal starting materials, and therefore do not require the detailed inspections and regulations of animal-derived materials. In one aspect, this invention is thus directed to bile acid pharmaceutical compositions free of material of animal origin, such as mammalian pathogens, as well as being substantially free of toxins of bacterial origin, such as pyrogens. The present bile acid pharmaceutical compositions are optionally in salt form, and, further optionally contain a pharmaceutically acceptable diluent, excipient or carrier. Cations for salt preparation may be selected from the group consisting of sodium ($Na^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH_4^+$). Salts may also be prepared from an alkali metal or an alkaline earth metal. An alkali metal may be selected from among sodium ($Na^+$), potassium ($K^+$), and lithium ($Li^+$). An alkaline earth metal may be selected from the group consisting of magnesium ($Mg^{2+}$), calcium ($Ca^{2+}$), barium ($Ba^{2+}$), and strontium ($Sr^{2+}$). Preferably for use as a pharmaceutical composition for localized removal of fat, the bile salt is sodium deoxycholate.

Prodrugs of the compounds of the embodiments are also contemplated. A prodrug is an active or inactive compound that is modified chemically through in vivo physiological action, such as hydrolysis, metabolism and the like, into a compound of the embodiments following administration of the prodrug to a patient. For example, one may prepare an ester of the present deoxycholic acid or derivatives thereof, so that the release of the deoxycholic acid or derivatives thereof is triggered by the disruption of the cell membrane, and release of esterase. With the release of esterase, the ester protecting group is cleaved so that the deoxycholic acid active form or derivatives thereof is present at the desired location in situ. For a general discussion of prodrugs involving esters see Svensson and Tunek Drug Metabolism Reviews 165 (1988) and Bundgaard Design of Prodrugs, Elsevier (1985), herein entirely incorporated by reference.

In general, the compounds of preferred embodiments will be administered in a therapeutically effective amount by any of the accepted modes of administration for agents that serve similar utilities. The actual amount of the compound of preferred embodiments, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

The compositions can be comprised of a disclosed compound in combination with at least one pharmaceutically acceptable excipient. Acceptable excipients are non-toxic, aid administration, and do not adversely affect the therapeutic benefit of the disclosed compound. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, vegetable or synthetic origin, e.g., peanut oil, soybean oil, mineral oil, sesame oil, etc. Preferred liquid carriers, particularly for injectable solutions, include water, saline, aqueous dextrose, and glycols.

The amount of the compound in a formulation can vary within the full range employed by those skilled in the art. The present compositions in various aspects as described herein may be prepared wherein the deoxycholic acid moiety is in the range of about 0.5%-10% on a weight per aqueous volume basis, or, on a w/w basis assuming the density of water (i.e., a 1:1 correspondence between weight and volume). In another aspect, the present embodiments relate to the presently described pharmaceutical compositions in concentrations up to saturation point of the diluent. One may select the degree of thixotropic viscosity based on conditions such as concentration and pH. See, e.g., Mukhopadhyay, S, and U. Maitra, Current Science 87: 1666-1683 (2004) at 1680.

Of particular note is the potential for local irritation upon injection of a bile acid composition of the present embodiments, and thus it may be desirable to administer, simultaneously or in seriatim, a local anesthetic. For example, lidocaine is frequently used in humans, and may be administered either as a co-formulation (in the same container and injected at the same time) or co-injection (injected from a different container). Anesthetics such as lidocaine may be administered via topical preparation, such as a patch or ointment.

For deeper tissue, anesthetics may be more deeply injected into the subject tissue or administered systemically (e.g., general anesthesia, epidural or other known methods).

The bile acid(s) or bile salt(s) in a solution of the invention can be at a concentration of about 0.001 to 10, 0.01 to 5, or 0.1 to 2% w/w, w/v, or v/v. Preferably, the bile acid(s) or bile salt(s) in the above solution can be at a concentration of about 0.1-5% w/w or more preferably about 1% w/w. In some embodiments, the fat dissolving solution comprises up to 100, 50, 20, 10, 5, 2, 1, 0.5, 0.2, 0.05, 0.02, or 0.01 grams of the one or more detergents, bile acids and/or bile salts, deoxycholic acid or salts thereof or sodium deoxycholate.

In preferred embodiments, the solutions herein include no lipids, phospholipids, or phosphatidylcholine. In some embodiments, the solutions herein include up to 5% w/w, w/v, or v/v lipids, phospholipids, or phosphatidylcholine.

In some embodiments, the above solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents. In some embodiments, a solution is in a container that contains up to 500 mL of solution. Such container can be a syringe or syringe-loadable container.

In some embodiments, compositions and methods further comprise a molecule known to cause fat to die by an orthogonal mechanism. Such molecules include neuropeptide Y (NPY) antagonists including, but not limited to, NPY receptor antagonists, such as BIBP-3226 (Amgen), BIBO-3304 (Boehringer Ingleheim), BMS-192548 and AR-H040922 (Bristol-Myers Squibb), LY-357897 (Eli Lilly), 1229U91 and GW438014S (GlaxoSmithKline), JNJ-5207787 (Johnson & Johnson), Lu-AA-44608 (Lundbeck), MK-0557 (Merck NPY), NGD-95-1 (Neurgogen), NLX-E201 (Neurologix), CGP-71683 (Novartis), PD-160170 (Pfizer), SR-120819A, BIIE0246, and S.A.0204 (Sanofi Aventis), S-2367 (Shiongli), dihydropyridine and dihydropyridine derivatives that are NPY receptor antagonists, bicyclic compounds that are NPY receptor antagonists, carbazole NPY receptor antagonists, and tricyclic compounds that are NPY receptor antagonists. See, e.g., WO 2006/133160 and U.S. Pat. No. 6,313,128 (incorporated herein by reference in its entirety including figures). Also contemplated are fat selective pro-apoptotic peptides such as the CKGGRAKDC peptide that homes to white fat vasculature. See, Kolonin M. G. et al., Nat. Med. June 10(6):625-32 (2004).

In some embodiments, the administering step involves delivering the compositions herein via a dermal patch, a pump, or subdermal depot. In some embodiments, the administering step involves delivering the compositions herein topically or subcutaneously. In specific embodiments, the administration step involves administering locally (e.g., subcutaneously or subdermally) to a region under eye, under chin, under arm, buttock, calf, back, thigh, or stomach of said subject. The administration can be made by a subcutaneous or transdermal injection.

In one aspect, the present invention relates to methods for reducing a subcutaneous fat deposit in a subject. Such methods comprise the step of administering locally to a subcutaneous fat deposit in the subject a composition comprising: (i)

a fat-dissolving effective amount of one or more pharmacologically active detergents, or bile acid(s) and/or bile salt(s), or deoxycholic acid or a salt thereof, or sodium deoxycholate; (ii) a pharmaceutical, veterinary, or cosmetic excipient; and (iii) optionally a lipid, wherein the ratio of the lipid and bile acid or bile salt is up to 1% w/w and wherein the composition does not include lipase or colipase. In some embodiments, the fat deposit is associated with a condition selected from the group consisting of obesity, fat redistribution syndrome, eyelid fat herniation, lipomas, Dercum's disease, lipodystrophy, buffalo hump lipodystrophy, dorsocervical fat, visceral adiposity, breast enlargement, hyperadiposity, diffused body fat around trunk and arms, and fat deposits associated with cellulite. In preferred embodiments, the above method does not include performing surgery on said subject.

In one aspect, the present invention relates to methods for reducing the appearance of a skin condition in a skin region of a subject. Such methods comprise the step of: administering locally to said skin region a composition comprising: (i) a skin-tightening effective amount of one or more pharmacologically active detergents, or bile acid(s) and/or bile salt(s), or deoxycholic acid or a salt thereof, or sodium deoxycholate, (ii) a pharmaceutical, veterinary, or cosmetic excipient, and (iii) optionally a lipid. In some embodiments, the administering step involves delivering the compositions herein via a subcutaneous or transdermal injection. In some embodiments, the skin condition being treated or ameliorated is selected from the group consisting of: loose skin, skin aging, irregularities of the skin, and wrinkles. In some embodiments, the region of skin being treated is under eye, under chin, under arm, buttock, cheek, brow, calf, back, thigh, ankle, or stomach.

In some embodiments, the compositions used for reducing the appearance of a skin condition in a skin region are formulation into a skin tightening solution. Such skin tightening solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and antidiarrhea agents.

In preferred embodiments, the detergent comprises a bile acid selected from the group consisting of deoxycholic acid, cholic acid, chenodeoxycholic acid, 7-alpha-dehydroxylate chenodeoxycholic acid, lithocholic acid, ursodeoxycholic acid, dihydroxytaurin acid, trihydroxytaurine acid, and glycine conjugates of any of the above. In some embodiments, the detergent comprises a bile salt that includes a cation selected from the group consisting of sodium ($Ni^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH_4^+$). In some embodiments, the detergent comprises a bile salt with a cation that is an alkali metal or an alkaline earth metal. Preferably, the alkali metal is sodium ($Na^+$), potassium ($K^+$), or lithium ($Li^+$) and the alkaline earth metal is magnesium ($Mg^{2+}$), calcium ($Ca^{2+}$), barium ($Ba^{2+}$), or strontium ($Sr^{2+}$). More preferably, the bile salt is sodium deoxycholate.

Sodium deoxycholate is a naturally produced bile salt that solubilizes dietary lipids in the digestive tract. It is produced in vivo via a complex biosynthetic route utilizing cholesterol as the starting material and involving both human and bacterial enzymes. The primary function of deoxycholate is to assist in the digestive process by solubilizing dietary lipids to facilitate absorption. In the body, deoxycholate biosynthesis begins with the enzymatic oxidation, isomerization, and reduction of cholesterol in the liver to form cholic acid, a bile acid structurally similar to its cholesterol parent (Stryer L, *Chapter 27: Biosynthesis of Membrane Lipids and Steroids*, in *Biochemistry*, 1995, W. H. Freeman and Company: New York. p. 691-707). In the liver, cholic acid is then chemically linked to one of two amino acids (taurine or glycine) to form the 'conjugated' cholic acids (i.e., L-glycocholate and taurocholate). These conjugated cholic acids are then stored in the gall bladder until food consumption. After food consumption, bile solution is released from the gall bladder into the intestine, where the conjugated cholic acid molecules are subject to two additional chemical modifications mediated by enzymes produced by intestinal microflora (Ridlon J. M., Kang D. J. and Hylemon P. B., *Bile salt biotransformation by human intestinal bacteria*, J. Lipid Res., 2006, 47(2): p. 241-59). First, conjugated cholic acid is dehydroxylated to form conjugated deoxycholate. Conjugated deoxycholate is then deconjugated to form free deoxycholate, which participates, along with the other bile acids, in the solubilization of dietary lipids. Because deoxycholate is downstream from cholic acid synthesis, cholic acid may be an impurity present in natural sources of deoxycholate.

Deoxycholate is soluble to 333 mg/mL in water, sparingly soluble in alcohol, and is even less soluble in acetone and glacial acetic acid. Reversible formation of micelles may occur with sodium deoxycholate concentrations above the critical micelle concentrations of approximately 2.4 mg/mL and neutral pH (Matsuoka K, M. Y., *Micelle formation of sodium deoxycholate and sodium ursodeoxycholate (part 1)*, Biochim. Biophys. Acta., 2002, 1580(2-3): p. 189-99). At concentrations above the critical micelle concentration of 2.4 mg/mL, deoxycholate will form micelles and has the ability to solubilize cells, lipids, and proteins. At lower concentrations such as 0.4 mg/mL (comparable to the fasting state), deoxycholate is 98% bound to albumin (Roda A. et al., *Quantitative aspects of the interaction of bile acids with human serum albumin*, J. Lipid Res., 1982. 23(3): p. 490-5) in the presence of 26 mg/mL of albumin (which is close to the serum physiological concentration of 35-50 mg/mL).

The preferred embodiments are directed to deoxycholic acid (DCA) or a pharmaceutically acceptable salt thereof and the related compositions and methods, wherein deoxycholic acid (DCA) is:

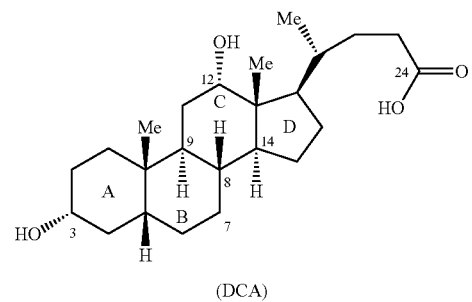

(DCA)

wherein said compound is not isolated from a mammalian or microbial organism naturally producing DCA.

Other preferred embodiments also are directed to stereoisomers of DCA and pharmaceutically acceptable salts thereof and to intermediates in the synthesis of the DCA and its stereoisomers and salts and the related compositions and methods.

Methods for complete chemical synthesis of bile acid pharmaceutical compositions, and useful intermediates, are now provided.

These following descriptions and examples provide an alternative to the extraction of DCA from mammalian or microbial organisms that naturally produce this compound. Synthetic routes 1-6 are contemplated for use in the present invention to synthesize deoxycholic acid (DCA). Synthetic route 1B and Examples 1-11 show the synthesis of DCA from hydrocortisone.

1. Synthetic Route #1A from Adrenosterone, Via 9(11)-ene or 11,12-ene

Cortisone (Compound 1.1) of Scheme 1A (below) is widely available as a fully synthetic material. It can be efficiently cleaved to form the $C_{17}$ ketone compound using pyridinium chlorochromate (PCC). This cleavage to adrenosterone (Compound 1.2) can also be achieved using $HIO_4$ or sodium bismuthate ($NaBiO_3$). The reaction that converts Compound 1.2 to Compound 1.3 is a known chemical process. Conversion of Compound 1.3 into Compound 1.4 involves monoketalization. Subsequent steps are regeneration of the 3-keto-4-ene, selective reduction of the 4,5-ene ($H_2$/Pt/DMF) to yield the $C_5$ β-configuration and selective reduction of the $C_3$ carbonyl group to the desired 3α-configuration to yield compound 1.5. The addition of a protecting group in converting Compound 1.5 into Compound 1.6 and subsequent reduction of the product yields the $C_{11}$ β-ol (axial configuration), i.e., compound 1.7, which is suitable for regioselective elimination to the key 9(11)-ene (i.e., conversion of Compound 1.7 into Compound 1.8).

The synthetic scheme bifurcates here, in that Compound 1.7 can be used as the starting material for conversion to either Compound 1.8 or Compound 1.9. The elimination reaction used to convert Compound 1.7 into Compound 1.8 is regioselective because of the trans diaxial relationship between the $C_{11}$ hydroxyl group and $C_9$ hydrogen atom. The alternative mode of elimination to yield the isomeric $C_{11}$-$C_{12}$ olefin of compound 1.9 is likewise regioselective involving cis-thermal elimination (i.e., conversion of Compound 1.7 to Compound 1.9).

Scheme 1A. Synthesis of the two C-ring precursors of the $C_{12}$ hydroxyl group of DCA

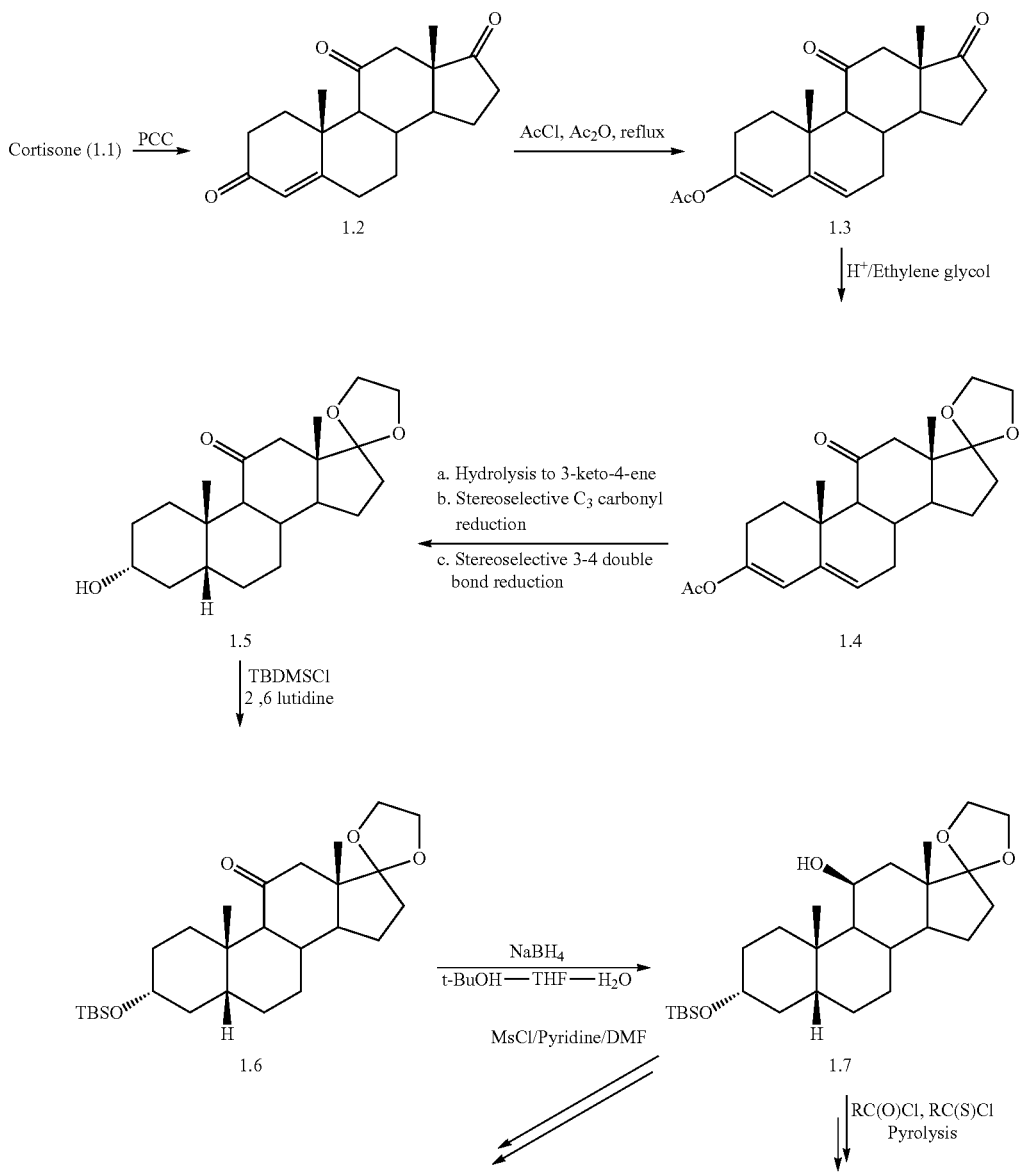

-continued

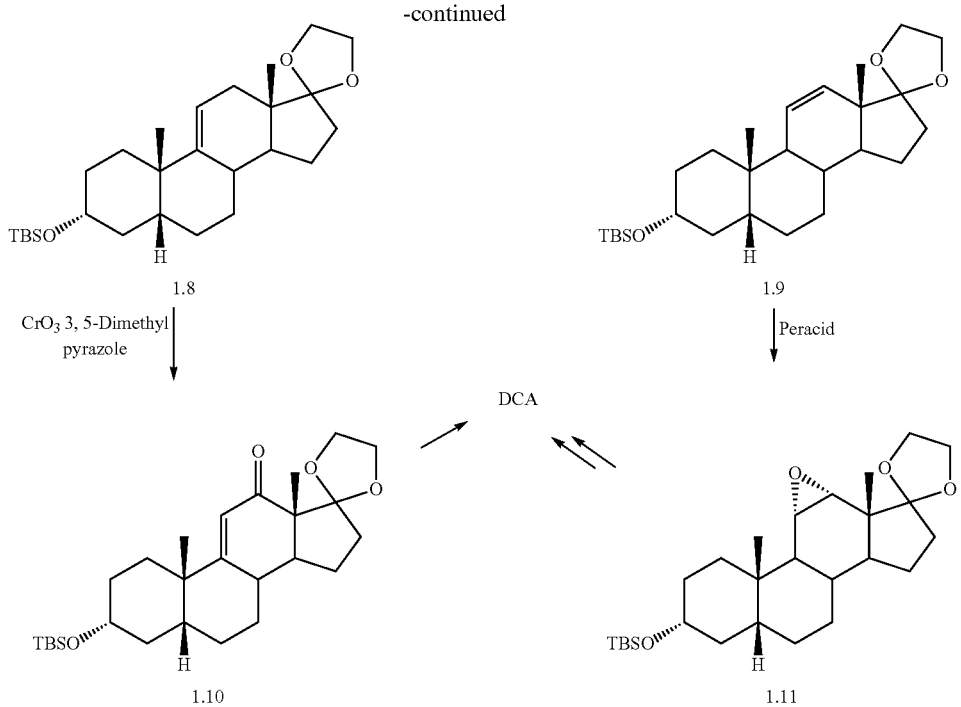

Allylic oxidation of Compound 1.8 (via treatment with $CrO_3$ and 3,5 dimethylpyrazole) yields the enone-containing Compound 1.10. Peracid oxidation of Compound 1.9 proceeds stereoselectively from the alpha-face of the steroid to yield the $C_{11-12}$ epoxide Compound 1.11 (see Scheme 1A above). These chemical transformations yield the two key precursors of the $C_{1-2}$ hydroxyl group functionality, namely, Compound 1.10 and Compound 2.1 (Schemes 1A and 2).

One of the skill in the art will appreciate that the above cortisone route can be modified to begin instead with hydrocortisone, which has the same carbon skeleton and the same relative placement of oxygen atoms, with hydrocortisone differing from cortisone only in the oxidation state of the C-11 oxygen bearing carbon atom. Hydrocortisone is commercially available and various synthesis of this compound are known (Szczebara et. al. Nature Biotechnology Vol. 21, Feb. 2003, 143-149) including a total chemical synthesis (Woodward R. B. et. al. 1952, J. Am. Chem. Soc. 74: 4223). Ketone 1.13 is synthesized starting from hydrocortisone 1.12 (Scheme 1B) via hydrogenolysis of the α, β-unsaturated double bond, followed by global ketone reduction using sodium borohydride to allow for 1,2-diol cleavage using $NaIO_4$, thus forming the $C_{17}$ ketone on the D-ring of the steroidal ring system. Subsequent oxidation with pyridinium chlorochromate (PCC) yields 1.13. Treatment of 1.13 with K-SELECTRIDE® (potassium tri-sec-butylborohydride) followed by acetylation with acetic anhydride/pyridine gives protected alcohol 1.15. Subsequent olefination of 1.15 with a Wittig reagent provides alkene 1.16 that is then treated with methyl propiolate and ethyl aluminum dichloride to form diene 1.17. Following hydrogenation of both double bonds, ketone 1.18 is reduced and the resulting alcohol intermediate is eliminated upon treatment with $SOCl_2$ in pyridine to give alkene 1.19. Allylic oxidation of alkene 1.19 with $CrO_3$ and reduction of the double bond under hydrogenation conditions gives ketone 1.21. Removal of the acetate protecting group and oxidation of the resulting alcohol gives diketone 1.22. Reduction of 1.22 with $LiAlH(O'-Bu)_3$ and hydrolysis of the methyl ester yields DCA.

Scheme 1B. Synthesis of DCA from Hydrocortisone

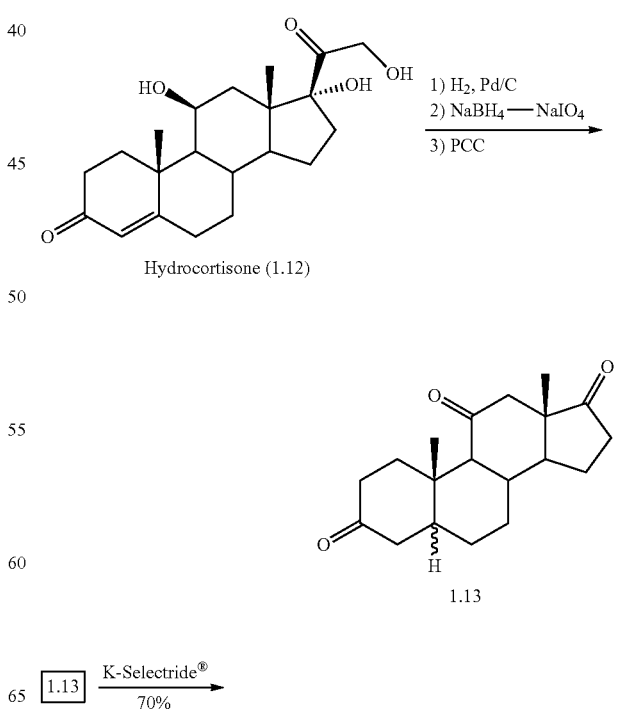

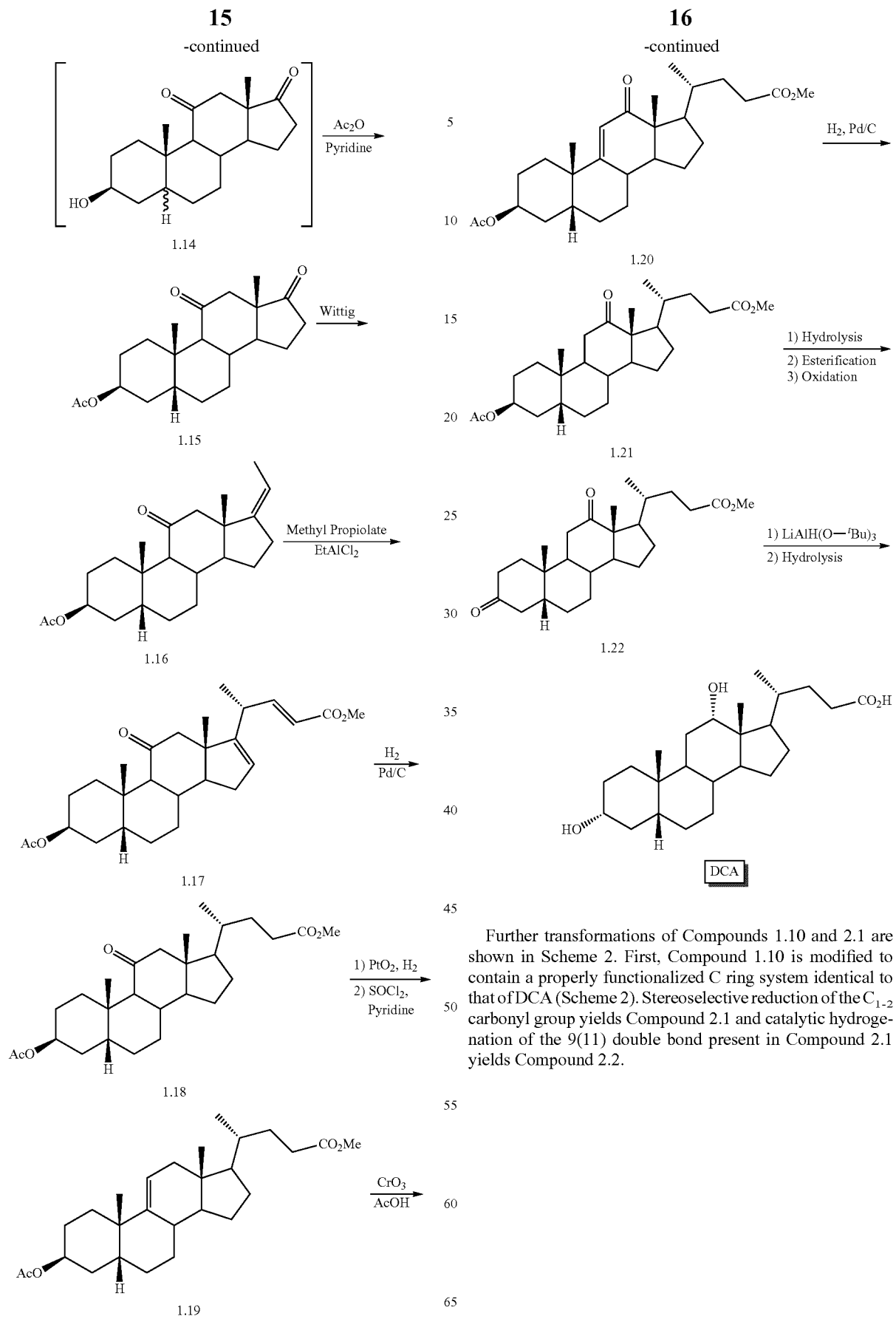
Further transformations of Compounds 1.10 and 2.1 are shown in Scheme 2. First, Compound 1.10 is modified to contain a properly functionalized C ring system identical to that of DCA (Scheme 2). Stereoselective reduction of the $C_{1-2}$ carbonyl group yields Compound 2.1 and catalytic hydrogenation of the 9(11) double bond present in Compound 2.1 yields Compound 2.2.

Scheme 2. Introduction of $C_{12}$ a hydroxyl group using the allylic oxidation route

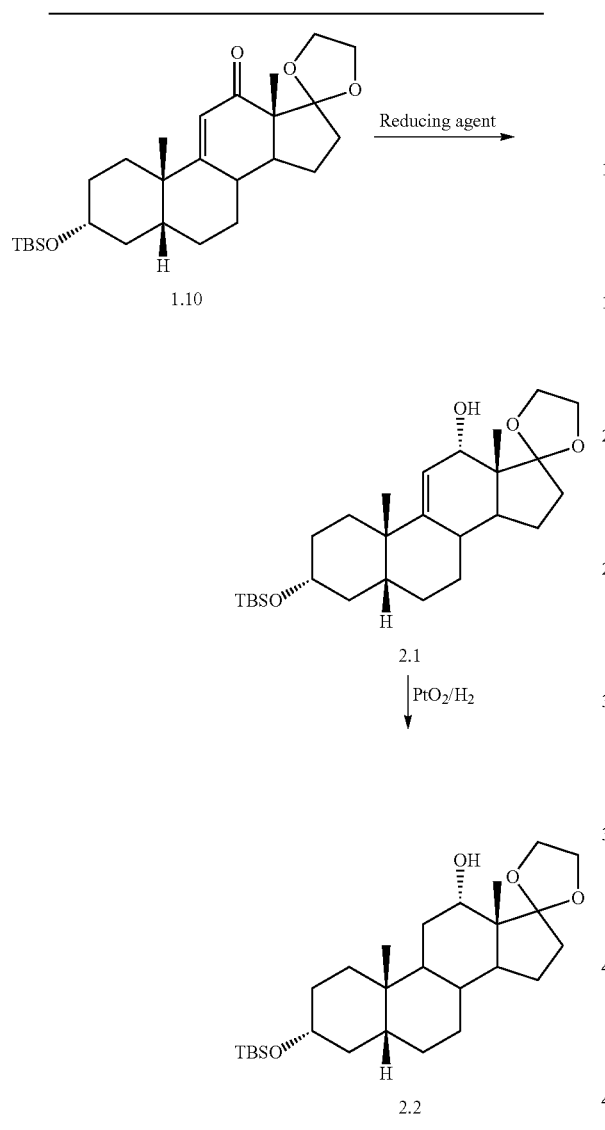

Scheme 3 presents the transformation of epoxide-containing Compound 1.11 to the analogous $C_{12}$ α-hydroxy steroid Compound 2.2 of Scheme 2.

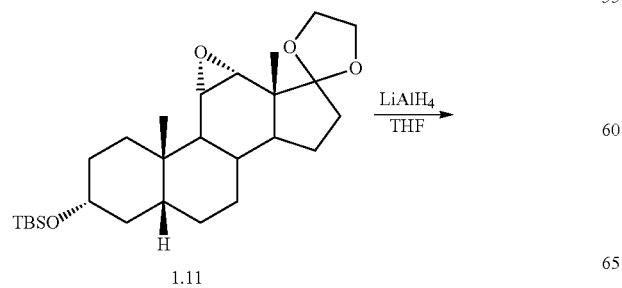

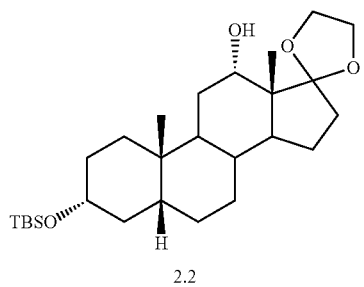

As mentioned above in both of these routes common intermediate compound 2.2 is formed.

The next step in the synthesis of DCA is the modification of the D-ring present in Compound 2.2 such that it contains the carboxylic side chain substituted D ring of DCA (Scheme 4 and Scheme 5).

Scheme 4. Deprotection and Wittig Reaction

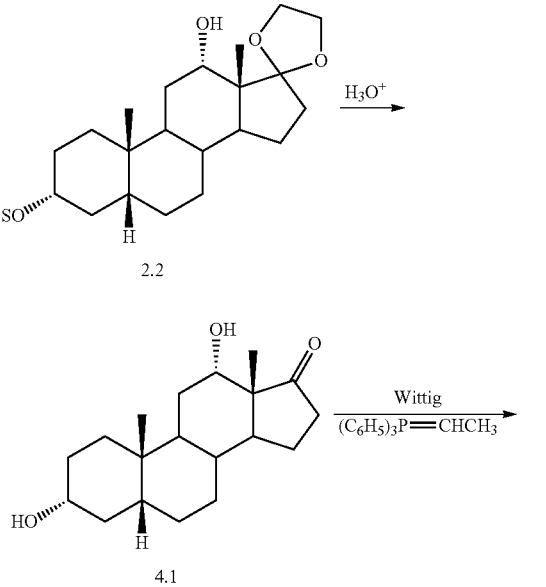

First the $C_{17}$ ketal and the $C_3$ silyl ether groups of Compound 2.2 are hydrolyzed. Then the Wittig reaction is performed to yield Compound 4.2. Conversion of Compound 4.2 to Compound 5.1 is carried out via an ene reaction. Subsequent catalytic reduction of Compound 5.1 and hydrolysis of the ester yields DCA (Scheme 5).

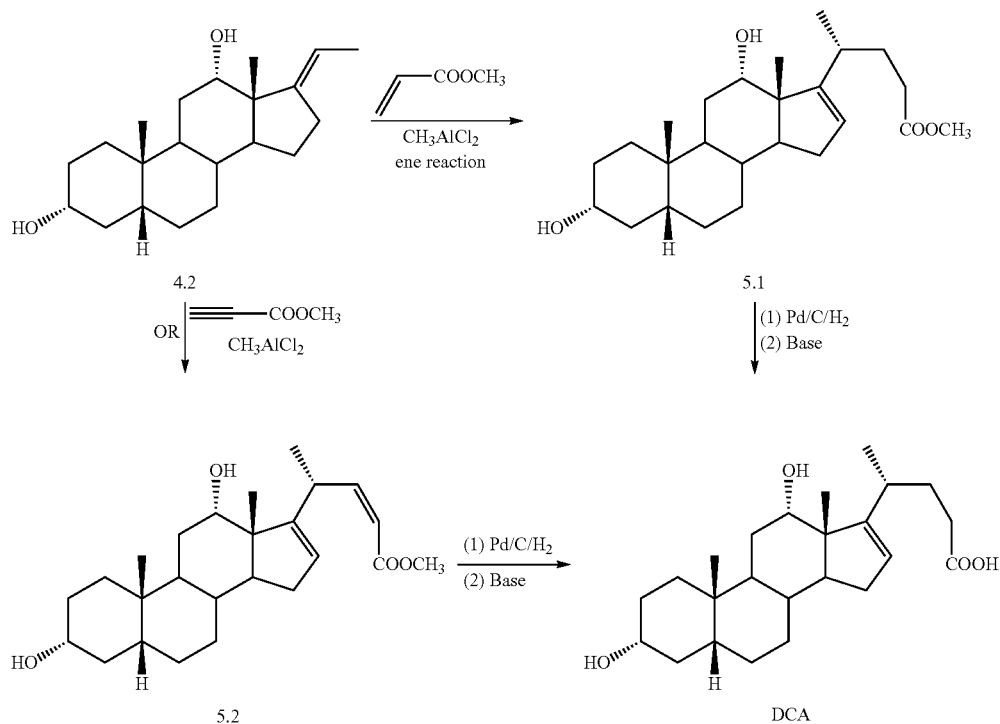

Scheme 5. Ene reaction and catalytic reduction for installation of DCA side chain

2. Synthetic Route #2 from Cortisone Via Adrenosterone (the i-Steroid, 3,5-cyclosterol Route)

Selective ketalization of adrenosterone (Compound 1.2, Scheme 6) at $C_{17}$, borohydride reduction, mesylation, and buffered hydrolysis yields the i-steroid (3,5-cyclosterol) containing Compound 6.1. Compound 6.1 undergoes 9(11)-ene formation (conversion of Compound 6.1 to Compound 6.2, Scheme 6) and allylic oxidation (conversion of Compound 6.2 to Compound 6.3, Scheme 6) followed by carbonyl group reduction to yield Compound 6.4. Hydrolysis of the i-sterol and hydrogenation yields Compound 6.5, which can be converted to DCA by synthetic methods presented above in Synthetic Route #1.

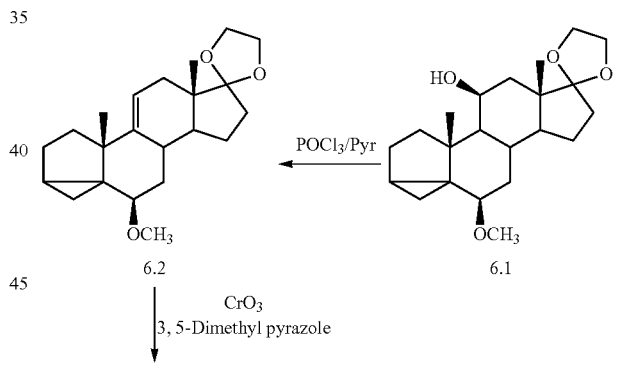

Scheme 6. Protection of A-B-ring system by formation of the i-steroid (i.e., 3, 5-cyclosterol)

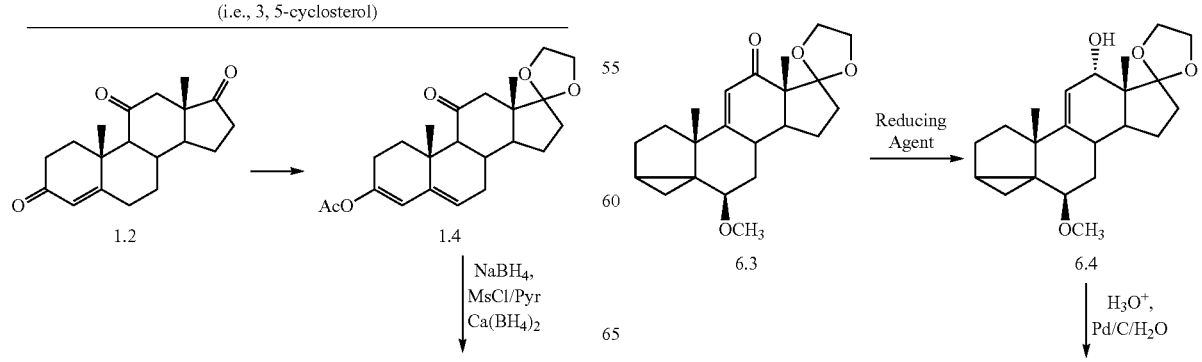

-continued

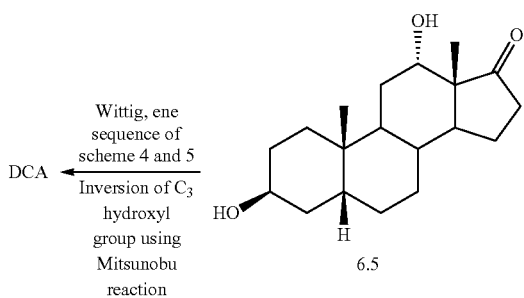

Wittig, ene sequence of scheme 4 and 5
DCA ← Inversion of $C_3$ hydroxyl group using Mitsunobu reaction 6.5

3. Synthetic Route #3 from Hecogenin

Hecogenin (Compound 7.1, Scheme 7) is a plant sterol found abundantly in Mexican yams and other plants of the Agave species. The central advantage of hecogenin as a starting material for DCA synthesis is that it possesses a $C_{12}$ oxygen functionality as is present in DCA.

The first step in the synthetic route starting from hecogenin is the stereoselective reduction of the $C_{1-2}$ carbonyl group in hecogenin (Compound 7.1) to the requisite $C_{12}$-α configuration (conversion of Compound 7.1 to Compound 7.2). Then the 3-β-ol, 5α-AB ring system is converted to the 3 α-ol, 5β-AB (Conversion of Compound 7.1, to Compound 7.2, to Compound 7.3) ring system (Scheme 7). The well-known Marker degradation (Marker, R. E., Rohrmann, E., *Sterols. LXIX. Oxidation Products of Sarsasapogenin. Sarsasapogenoic Acid and Related Substances*, J. Am. Chem. Soc., 1939. 61(8): p. 2072-2077) follows the conversion of Compound 7.2 to Compound 7.3 to yield Compound 7.4. Installation of the D-ring side chain (Scheme 8) into Compound 8.2 is achieved via methods shown in Schemes 4 and 5. The requisite $C_{17}$ ketone in Compound 8.2 is formed by ozonolysis of the enol acetate of Compound 8.1 (Scheme 8). DCA is then prepared from 8.2 in a similar manner as in Scheme 5 using the olefination and ene reaction sequence. Alternative routes starting from starting from hecogenin are shown in Schemes 9 and 10.

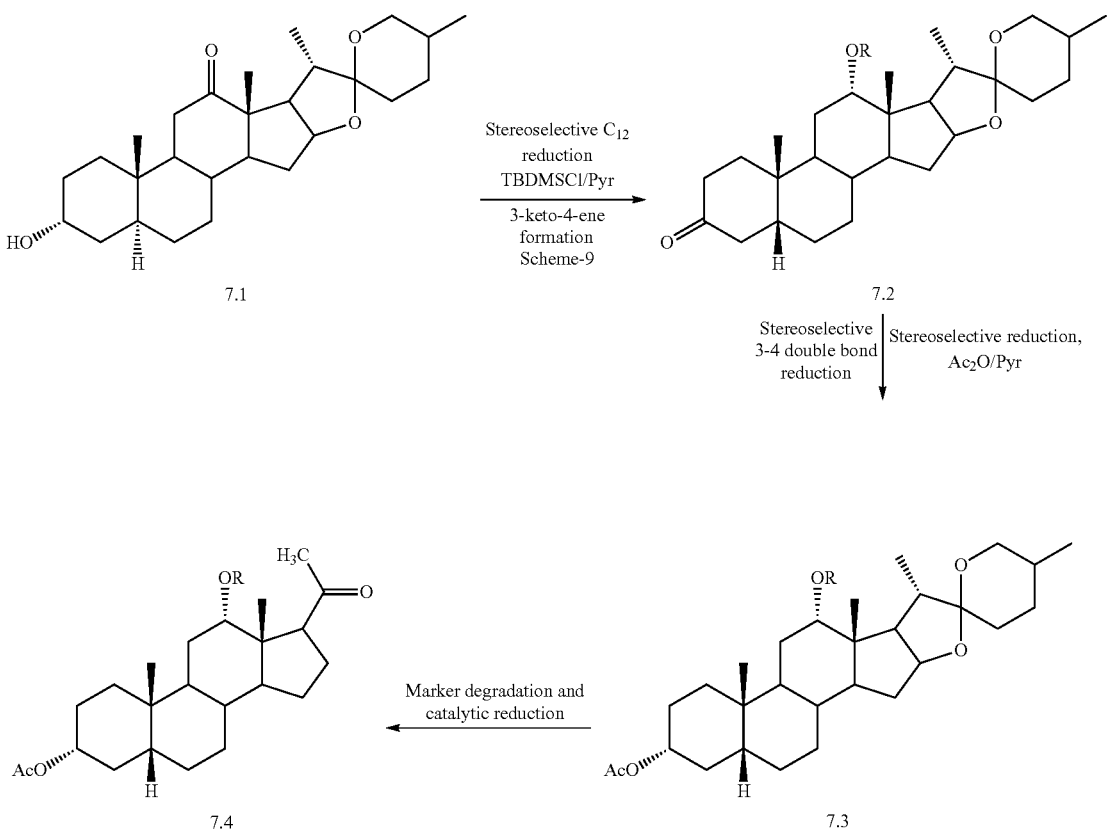

Scheme 7. $C_{12}$-hydroxyl group introduction, AB ring modification and side chain cleavage

R = TBDMS

Scheme 8. Side-chain introduction
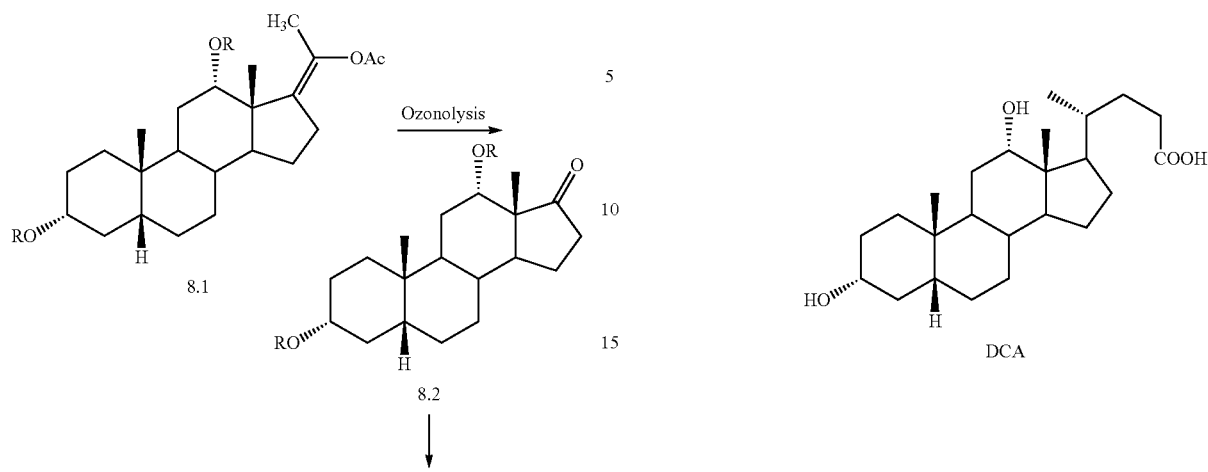
-continued
Scheme 9. Dithioethane route to 3-keto-4-ene
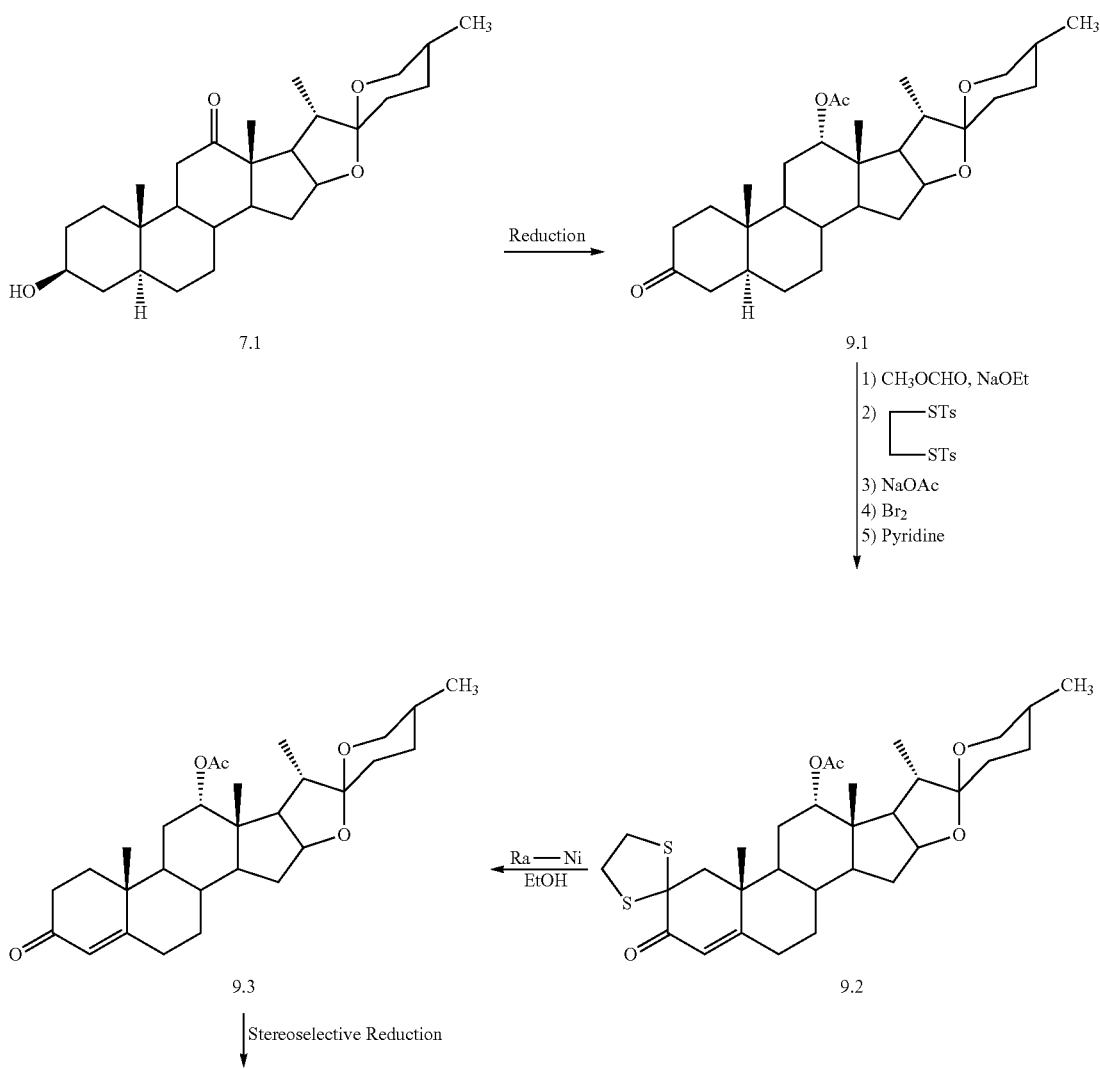

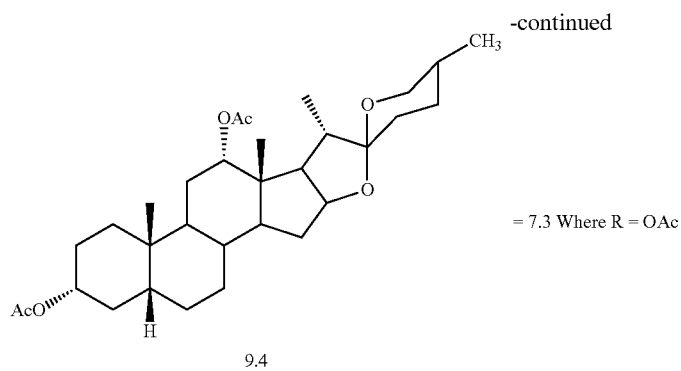

9.4

Scheme 10A. Formation DCA via the 3-keto-4-ene

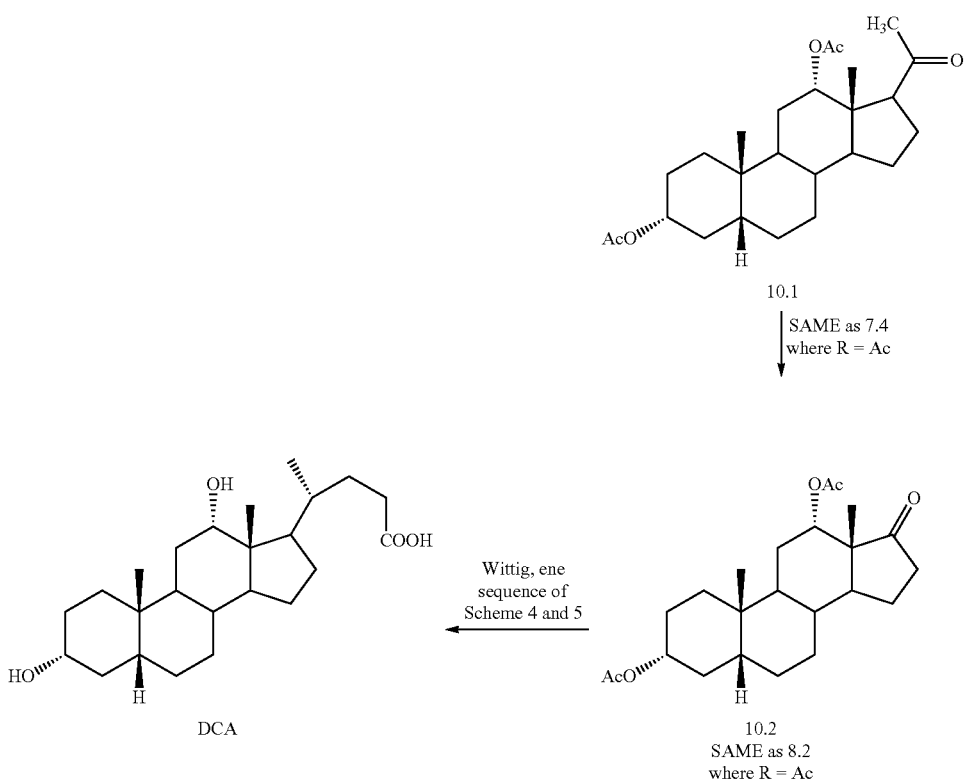

4. Synthetic Route #4 from Sapogenins

Sapogenins are derived from the hydrolysis of the saccharides and disaccharides attached to the $C_3$ hydroxyl group of the saponins (i.e., steroid glycosides). These are widely occurring plant products. Saponin occurs in nature as a spiroketal structure as shown below. Also Compound 10.3 can be formed from tigogenin, diosgenin, chlorogenin, smilagenin and hecogenin (Compound 7.1). We believe that DCA could be synthesized from each of these, namely, tigogenin, diosgenin, chlorogenin, smilagenin and hecogenin (Compound 7.1). (Y. Mazur, N. Danieli and Franz Sondheimer J. Am. Chem. Soc.; 82, 5809, 1960).

Since we could synthesize DCA from hecogenin, we recognize that any of the above sapogenins could, likewise, serve as a starting material for DCA synthesis.

Scheme 10B. Synthetic route from saponin.

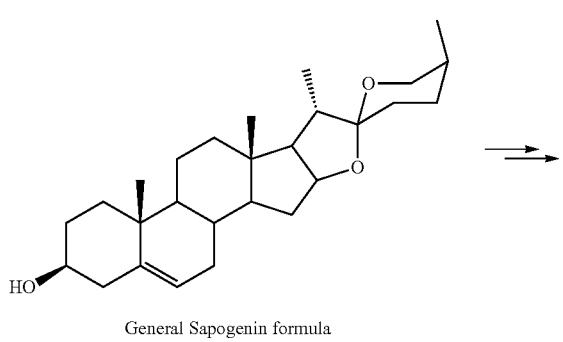

General Sapogenin formula

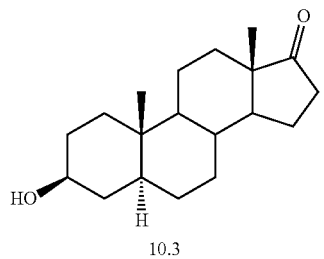

10.3

5. Synthetic Route #5 from Stigmasterol

Stigmasterol (Compound 11.1) is a widely available plant sterol. As a starting material for the DCA synthesis, it has an advantage in that it contains a functionalized AB ring system and a readily cleavable side chain moiety. It has the disadvantage in that it lacks the required functionality in the C ring essential for DCA synthesis.

In this synthetic route, the stigmasterol (Compound 11.1) AB ring is protected by i-steroid formation followed by ozonolysis to yield a side-chain at $C_{17}$ installed and reduced to the $C_{24}$-ol as a masked form of the carboxyl group (Scheme 11). The subsequent steps generate an allylic position at $C_{12}$ (Scheme 12). The B-ring diene formation and mercuric acetate oxidation are known processes and catalytic reduction of the B ring system yields an intermediate common with previous routes described above. However, in contrast to other routes, the side chain is already present. Allylic oxidation (conversion of Compound 12.4 to Compound 1.20) and stereoselective reduction (conversion of Compound 1.20 to Compound 1.21) followed by previously discussed steps, yields a product which is converted to DCA.

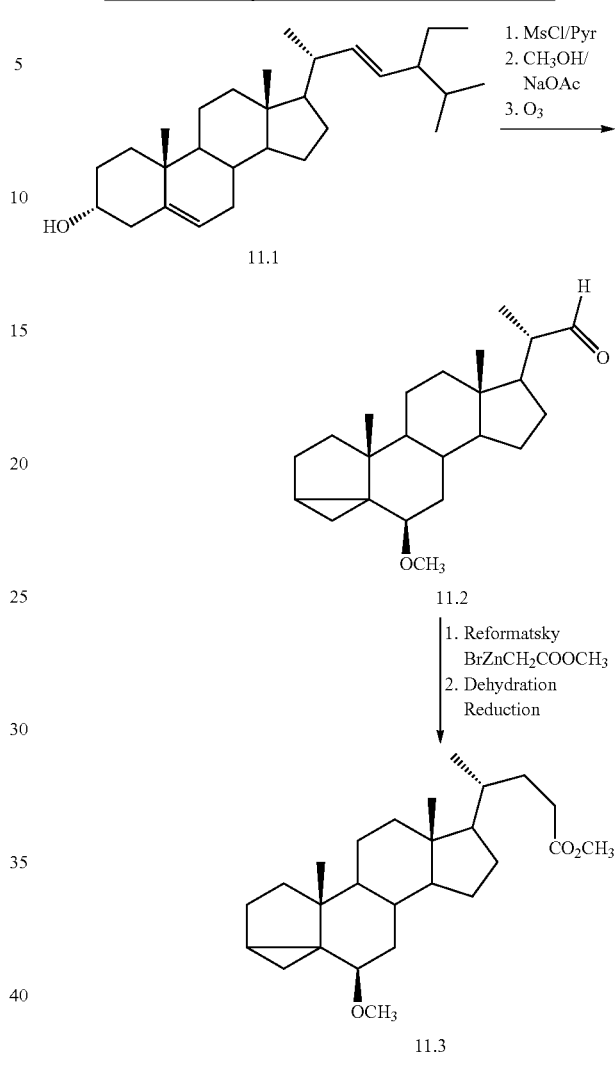

Scheme 11. Ozonolysis of i-steroid and side chain reduction

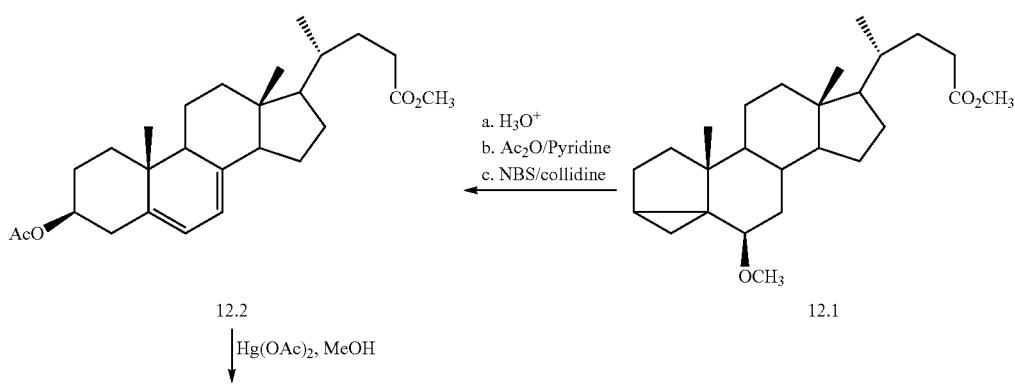

Scheme 12. Triene formation and allylic oxidation

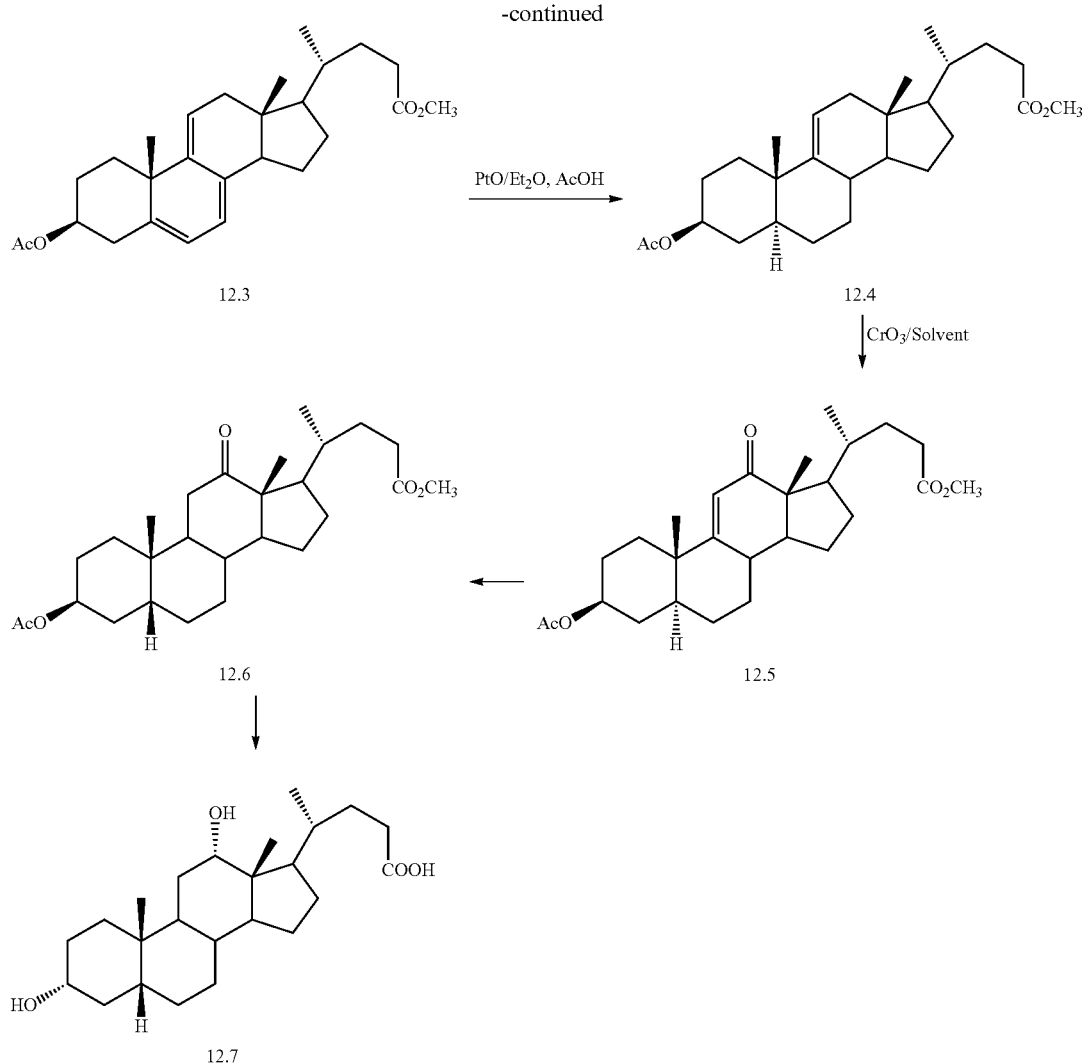
A variation of the stigmasterol route uses the Diels-Alder protection of the B-ring diene. This is advantageous because it isolates the 9(11) double bond to prevent possible interference during the allylic oxidation steps (Scheme 13).
Scheme 13. Triene Formation and Diels-Alder Protection of the Ring B Diene.
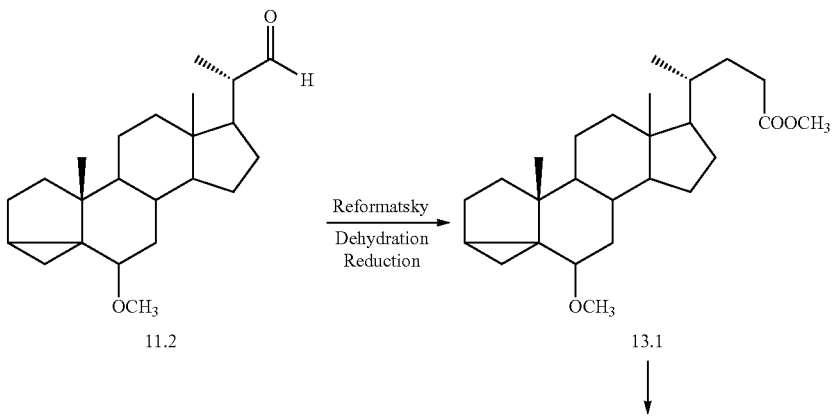

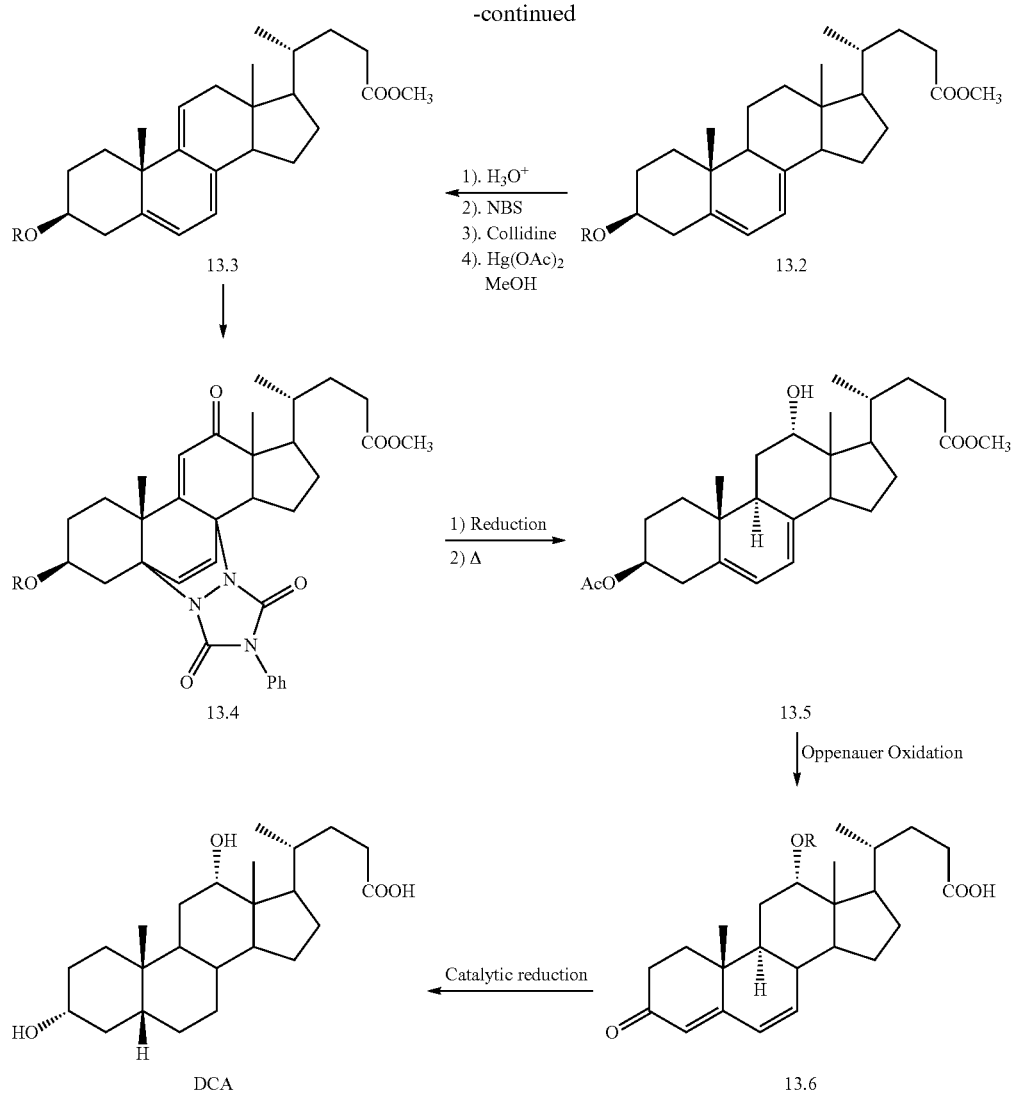

6. Synthetic Route #6 from Ergosterol

Ergosterol (Compound 14.1) is a readily available starting material and can be used to prepare DCA by adaptation of the procedures set forth in this application.

Allylic oxidation offers a facile route to $C_{12}$ oxygen functionality (Scheme 14). This route has the advantage of starting with the ring B diene. It is convergent with the stigmasterol route.

Scheme 14. Triene formation from Ergosterol

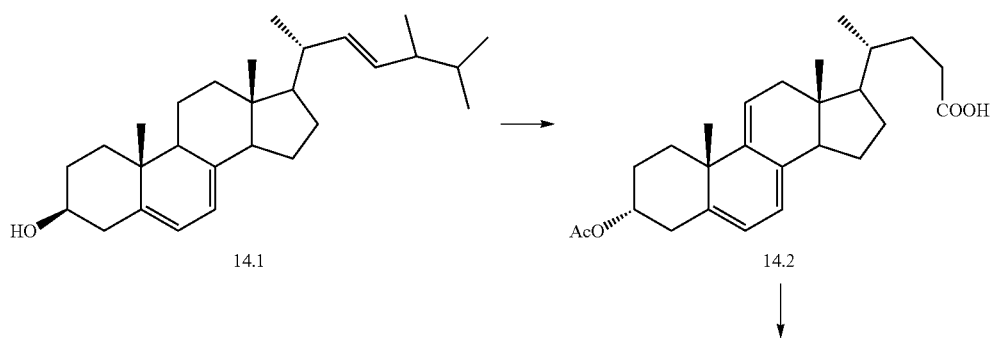

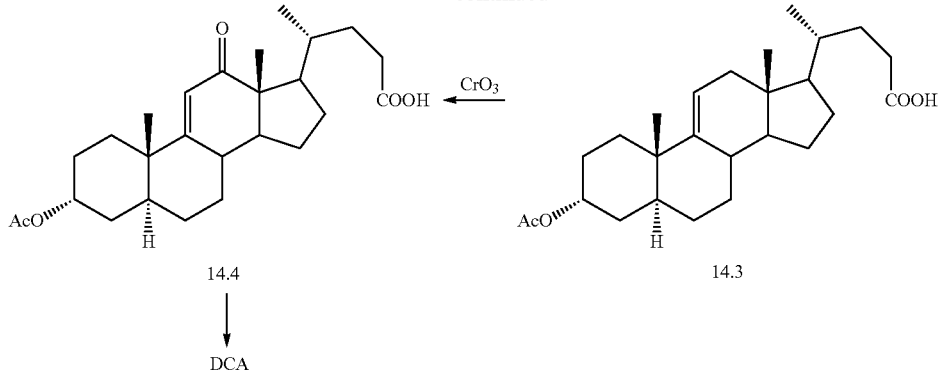

14.4 ← CrO₃ ← 14.3

↓

DCA

Another embodiment provides for a method for removal of fat deposits from selected locations in a mammal comprising administering to the mammal in need thereof a therapeutically effective amount of a compound that is DCA or pharmaceutically acceptable a salt thereof,

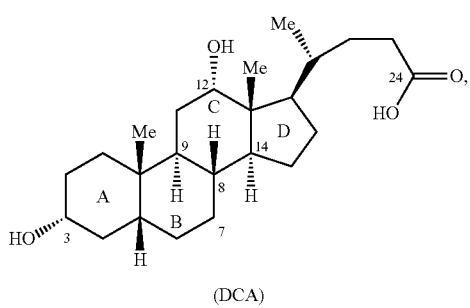

(DCA)

wherein said compound is not isolated from a mammalian or microbial organism naturally producing DCA.

Another embodiment provides for a method of emulsifying fat in a mammal comprising administering to the mammal in need thereof a therapeutically effective amount of a compound that is DCA or pharmaceutically acceptable a salt thereof,

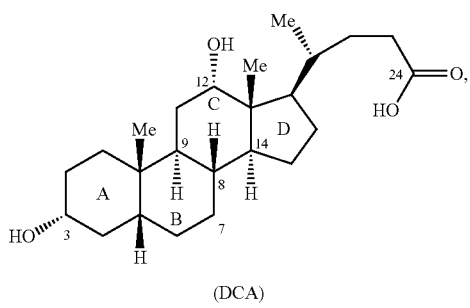

(DCA)

wherein said compound is not isolated from a mammalian or microbial organism naturally producing DCA.

Another embodiment provides for a method of solubilizing phosphatidylcholine comprising mixing phosphatidylcholine and effective amount of a compound that is DCA or pharmaceutically acceptable a salt thereof,

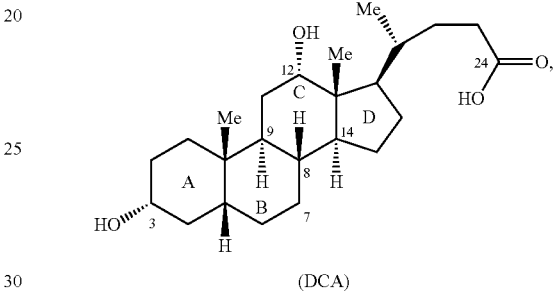

(DCA)

wherein said compound is not isolated from a mammalian or microbial organism naturally producing DCA.

Another aspect of the invention relates to mixing adipo-ablative bile acids, such as, deoxycholic acid (DCA) with agents that kill fat cells. In one aspect, this invention contemplates a means to enhance the aesthetic effects of deoxycholate injections by mixing into the deoxycholate injectate a molecule that causes fat to die by an orthogonal mechanism. Examples of such candidate molecules include, but are not limited to, neuropeptide Y (NPY) antagonists and fat selective pro-apoptotic peptides. Since both fat cell killing and skin tightening may be required to mediate the desired effects, the effects of an agent with fat killing ability and potent skin tightening effects (such as deoxycholate) can be enhanced via the addition of a molecule with potent fat cell killing effects. Additionally, molecules that require access to the vasculature to kill (such as certain pro-apoptotic peptides that bind to proteins expressed on the luminal side of capillaries) can gain access to these proteins because deoxycholate may cause vascular leakage. Thus, such agents can be synergistic with deoxycholate potentially creating a more potent means to mediate body contouring in fewer therapeutic sessions.

Examples of NPY antagonists include, but are not limited to, NPY receptor antagonists, such as BIBP-3226 (Amgen), BIBO-3304 (Boehringer Ingleheim), BMS-192548 and AR-H040922 (Bristol-Myers Squibb), LY-357897 (Eli Lilly), 1229U91 and GW438014S (GlaxoSmithKline), JNJ-5207787 (Johnson & Johnson), Lu-AA-44608 (Lundbeck), MK-0557 (Merck NPY), NGD-95-1 (Neurgogen), NLX-E201 (Neurologix), CGP-71683 (Novartis), PD-160170 (Pfizer), SR-120819A, BIIE0246, and S.A.0204 (Sanofi Aventis), S-2367 (Shiongli), dihydropyridine and dihydropyridine derivatives that are NPY receptor antagonists, bicyclic compounds that are NPY receptor antagonists, carbazole NPY receptor antagonists, and tricyclic compounds that are NPY receptor antagonists. See, e.g., WO 2006/133160 and U.S. Pat. No. 6,313,128 (incorporated herein by reference in its entirety including figures).

Exemplary fat selective pro-apoptotic peptides includes, but is not limited to, CKGGRAKDC peptide that homes to white fat vasculature. See, Kolonin M. G. et al., Nat. Med. June 10(6):625-32 (2004).

The compounds of preferred embodiments can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

The starting materials and reagents for the reactions described herein are generally known compounds or can be prepared by known procedures or obvious modifications thereof. For example, many of the starting materials and reagents are available from commercial suppliers such as Aldrich Chemical Co. (Milwaukee, Wis., USA), Bachem (Torrance, Calif., USA), Emka-Chem or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the preferred embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

EXAMPLES

The various starting materials, intermediates, and compounds of the preferred embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Exemplary embodiments of steps for performing the synthesis of products in Synthetic Route #1, Scheme 1B is described in greater detail infra. Table 1 describes abbreviations used to express various compounds/moieties/apparatus/procedure/property in the exemplary reaction schemes and synthetic routes described in the following examples and throughout the specification.

TABLE 1

| | |
|---|---|
| AcOH | Acetic acid |
| CAN | Acetonitrile |
| $Ac_2O$ | Acetic anhydride |
| AcCl | Acetyl chloride |
| $NH_4Cl$ | Ammonium chloride |
| $CHCl_3$ | Chloroform |
| $CrO_3$ | Chromium trioxide |
| DCA | Deoxycholic acid |
| DCM ($CH_2Cl_2$) | Dichloromethane |
| DMF | N,N-Dimethylformamide |
| DMSO | Dimethyl sulfoxide |
| EtOAc | Ethyl acetate |
| $EtAlCl_2$ | Ethyl aluminum dichloride |
| Hz | Hertz |
| HPLC | High pressure liquid chromatography |
| HCl | Hydrochloric acid |
| LAH | Lithium aluminum hydride |
| LiOH | Lithium hydroxide |
| $MgSO_4$ | Magnesium sulfate |
| MHz | Megahertz |
| MeOH | Methanol |
| mmol | millimole |
| mL | milliliter |
| mol | mole |
| Obs | Observed |
| $HClO_4$ | Perchloric acid |
| $PtO_2$ | Platinum oxide |
| KBr | Potassium bromide |
| K-O$^t$Bu | Potassium tert-butoxide |
| PCC | Pyridinium chlorochromate |
| Rep | Reported |
| NaOH | Sodium hydroxide |
| THF | Tetrahydrofuran |
| $SOCl_2$ | Thionyl chloride |
| TEA | Triethylamine |
| TLC | Thin layer chromatography |
| Wt | Weight |

General:

Manipulations of oxygen- and moisture-sensitive materials are conducted with two-necked flame dried flasks under an argon atmosphere. Column chromatography is performed using SE-Make silica gel (60-120 Mesh), Spectrochem silica gel (230-400 Mesh) or aluminium oxide 90-neutral. (SD-Fine Chem. Ltd., India). Analytical thin layer chromatography (TLC) was performed on Merck Kieselgel 60 $F_{254}$ (0.25 mm) plates (Merck & Co., Whitehouse Station, N.J.). Visualization of spots was detected either by UV light (254 nm) lamp or by charring with a solution of sulfuric acid (5%) and p-anisaldehyde (3%) in ethanol.

Apparatus:

Analysis of the compounds and products of the reaction schemes and synthetic routes described herein may be performed on the apparatus and equipment described infra.

Nuclear Magnetic Resonance (NMR)

Proton and carbon nuclear magnetic resonance spectra ($^1$H NMR and $^{13}$C NMR) are recorded on a Varian Mercury-Gemini 200 ($^1$H NMR, 200 MHz; $^{13}$C NMR, 50 MHz) or a Varian Mercury-Inova 500 ($^1$H NMR, 500 MHz; $^{13}$C NMR, 125 MHz) (Varian, Inc., Palo Alto, Calif.) spectrometer with solvent resonances as the internal standards ($^1$H NMR, $CHCl_3$ at 7.26 ppm or DMSO at 2.5 ppm and DMSO-$H_2O$ at 3.33 ppm; $^{13}$C NMR, $CDCl_3$ at 77.0 ppm or DMSO at 39.5 ppm). $^1$H NMR data are reported as follows: chemical shift (δ, ppm), multiplicity (s=singlet, d=doublet, t=triplet, q=quartet, br=broad, m=multiplet), coupling constants (Hz), and integration.

Infrared Spectroscopy

Infrared spectra (FT-IR) are run on a JASCO-460+ model (Jasco, Inc., Easton, Md.). Mass spectra are obtained with a Perkin Elmer, API-2000 spectrometer (Perkin Elmer, Inc., Waltham, Mass.) using ES+ mode.

Melting Point

Melting points were determined using a LAB-INDIA melting point measuring apparatus (Labindia Instruments Pvt. Ltd., India) and are uncorrected.

High Pressure Liquid Chromatography

HPLC chromatograms were recorded using a SHIMADZU-2010 model with a PDA detector (Shimadza Corp., Japan).

Optical Activity

Specific optical rotations ($[\alpha]_D$) are determined employing a JASCO-1020 at 589 nm (Jasco, Inc., Easton, Md.) and are uncorrected.

Chemicals:

Unless otherwise noted, commercially available reagents are used without purification. Diethyl ether and THF are distilled from sodium/benzophenone ketyl. Anhydrous DMF, DCM, pentane and hexane are obtained by distillation from $CaH_2$.

Example 1

Preparation of Androstane-3,11,17-trione (1.13)

10% of Pd/C (2.5 g, 5 wt %) is added to a solution of hydrocortisone (Compound 1.12) (50.0 g, 138.12 mmol) in DMF (250 mL). The resulting slurry is hydrogenated in a Parr apparatus (50 psi) for 12 h. Upon complete disappearance of starting material, as evidenced by TLC, the crude reaction mixture is filtered through a small plug of Celite, and the solvent is removed under vacuum. Crude product (48.0 g) is obtained as a colorless solid.

$NaBH_4$ (2.1 g, 55.3 mmol) is added to a solution of the above crude product (48.0 g, 131.86 mmol) in EtOH (500 mL) and $CH_2Cl_2$ (500 mL). After 1 hr, acetone (50 mL) and water (150 mL) are added, followed by $NaIO_4$ (70.5 g, 329.6 mmol). The mixture is stirred at room temperature overnight.

Distilled water (500 mL) is added and the mixture is extracted with ethyl acetate (3×250 mL). The ethyl acetate layer is flushed through a silica-gel plug and the solvent is evaporated to yield 38 g as a colorless solid. The crude product is oxidized further without purification.

PCC (40.4 g, 187.5 mmol) is added to a solution of the above crude product in $CH_2Cl_2$ (400 mL) in 3 equal portions over 30 minutes. The resulting reaction mixture is stirred at room temperature for about 3-4 h. Upon completion of the reaction, as monitored by TLC, the crude reaction mixture is filtered sequentially through pads of Celite and silica gel and the crude material is purified by column chromatography [59(W)×700 (L) mm, 60-120 Mesh silica, 150 g], eluting with ethyl acetate/hexane (3:10) [50 mL fractions, 10 mL/min elution, monitored by TLC with p-anisaldehyde charring; $R_f$ for Compound 1.13=0.37 and $R_f$ for Compound 1.12=0.05 in EtOAc/Hexane (1:1)] to provide the diastereomeric Compound 1.13 (33.0 g, 79% yield) as a colorless solid.

The obtained crude material was purified by preparative HPLC using a Phenomenex Lunov C18 column (250×30.0 mm, 10 g) and isocratic elution with $CH_3CN:H_2O$ (12:13) with a 25 mL/min flow rate in 15 mL fractions. The preparative HPLC is only used for purification, but not for analysis. Table 2 describes the measured properties of the product.

TABLE 2

| | |
|---|---|
| $^1$H NMR (500 MHz, $CDCl_3$) | δ = 2.76 (dt, J = 4.0, 15.0 Hz, 1H), 2.62-2.35 (m, 5H), 2.33-2.24 (m, 1H), 2.23-2.05 (m, 4H), 2.02-1.88 (m, 3H), 1.81 (bd, J = 14.0 Hz, 2H), 1.72-1.61 (m, 1H), 1.57-1.48 (m, 1H), 1.47-1.32 (m, 2H), 1.26 (s, 3H), 0.86 (s, 3H) |
| $^{13}$C NMR (125 MHz, $CDCl_3$) | δ = 216.9, 211.8, 208.4, 52.3, 50.3, 50.2, 50.0, 44.5, 41.9, 37.1, 36.0, 35.9, 35.8, 34.3, 25.6, 25.0, 22.2, 21.3, 14.5 |
| Mass (m/z) | 303.2 [M+ + 1], 320.1 [M+ + 18] |
| IR (KBr) | 3443, 2916, 1729, 1705, 1466, 1379, 1044 cm$^{-1}$ |
| m.p. | 128.9-131° C. (from $CH_2Cl_2$/Hexane) (observed); 128-131° C. (Rep. E. Caspi *J. Org. Chem.* 1959, 24, 669) |
| $[\alpha]_D$ | +139 (c = 1 in $CHCl_3$) |
| HPLC purity | 98.6%, ret. time = 16.61, (Hypersil BDS C18; 250 × 4.6 mm, 5u), ACN: 5 mM TEA pH-2.5 with $HClO_4$ (Gradient), absorbance at 205 nm |

Example 2

3β-Hydroxy-androstane-11,17-dione (1.14)

K-SELECTRIDE®(potassium tri-sec-butylborohydride) (98.39 mL, 98.01 mmol, 1M solution in THF) is added to a solution of Compound 1.13 (33.0 g, 109.27 mmol) in THF (330 mL) over 15 minutes under an inert atmosphere at −78° C. and is stirred for about 3-4 h at −78° C. The reaction mixture is quenched with aqueous NaOH solution (2M, 70 mL). The crude reaction mixture is diluted with ethyl acetate (500 mL) and the organic layer is washed with water (3 ×75 mL), saturated brine solution (100 mL) and dried over $MgSO_4$ (75 g). The solvent is removed under vacuum to afford 33 g of crude material. The crude product is subjected to acetylation without purification.

Purification of Crude Material

The crude material is purified by column chromatography [29(W)×600(L) mm, 230-400 Mesh silica, 200 g], eluting with ethyl acetate/hexane (1:4) [25 mL fractions, 5 mL/min elution, monitored by TLC with p-anisaldehyde charring; $R_f$ for Compound 1.14=0.3 and $R_f$ for Compound 1.13=0.37 in EtOAc/Hexane (1:1)] to afford Compound 1.14. Table 3 describes the measured properties of the product.

TABLE 3

| | |
|---|---|
| $^1$H NMR (500 MHz, $CDCl_3$) | δ = 4.08 (s, 1H), 2.53 (q, J = 9.0 Hz, 1H), 2.42 (d, J = 13.0 Hz, 1H), 2.34-2.21 (m, 3H), 2.11-2.04 (m, 1H), 1.98-1.91 (m, 3H), 1.88-1.59 (m, 6H), 1.57-1.26 (m, 6H), 1.21 (s, 3H), 0.82 (s, 3H) |
| $^{13}$C NMR (125 MHz, $CDCl_3$) | δ = 217.4, 209.1, 66.3, 51.6, 50.6, 50.5, 37.1, 36.2, 35.9, 34.8, 33.5, 28.8, 28.5, 25.7, 25.6, 23.6, 21.5, 14.5 |
| Mass (m/z) | 305.0 [M+ + 1], 322.0 [M+ + 18] |
| IR (KBr) | 3519, 2928, 1735, 1697, 1454, 1379 cm$^{-1}$ |
| m.p. | 176.6-180.5° C. |
| $[\alpha]_D$ | +125 (c = 1 in $CHCl_3$) |

Example 3

3β-Hydroxyandrostane-11,17-dione acetate (1.15)

Acetic anhydride (16.6 g, 162.8 mmol) is added to a solution of Compound 1.14 (33.0 g, 108.55 mmol) in pyridine (150 mL) at 0° C. under an inert atmosphere. The resulting reaction mixture is stirred overnight at ambient temperature. Upon completion of the reaction, as evidenced by TLC, pyridine and remaining acetic anhydride are removed under vacuum. The crude residue is diluted with ethyl acetate (500 mL) and washed with water (3×150 mL), saturated brine solution (100 mL) and dried over MgSO$_4$ (75 g). The solvent is evaporated under vacuum and the crude material is purified by column chromatography [59(W)×800(L) mm, 60-120 Mesh silica, 150 g], eluting with ethyl acetate/hexane (1:10) [25 mL fractions, 10 mL/min elution, monitored by TLC with p-anisaldehyde charring; R$_f$ for Compound 1.15=0.38 and R$_f$ for Compound 1.14=0.1 in EtOAc/Hexane (3:7)] to afford Compound 1.15 (19.0 g, 66.4% yield) as a colorless solid. Table 4 describes the measured properties of the product.

TABLE 4

| | |
|---|---|
| $^1$H NMR (500 MHz, CDCl$_3$): | δ = 5.03 (s, 1H), 2.53 (dd, J = 9.5, 19.0 Hz, 1H), 2.42 (d, J = 10.0 Hz, 1H), 2.36-2.31 (m, 3H), 2.25 (dd, J = 9.5, 19.0 Hz, 1H), 2.10-2.06 (m, 1H), 2.04 (s, 3H), 1.96-1.91 (m, 3H), 1.81-1.69 (m, 2H), 1.63-1.57 (m, 3H), 1.50 (dd, J = 3.0, 14.5 Hz, 1H), 1.36 (d, J = 9.5 Hz, 3H), 1.27-1.22 (m, 1H), 1.20 (s, 3H), 0.82 (s, 3H) |
| $^{13}$C NMR (125 MHz, CDCl$_3$) | δ = 217.2, 208.9, 170.4, 69.7, 51.5, 50.5, 50.4, 37.9, 36.1, 35.9, 34.5, 30.6, 29.6, 29.5, 25.5, 25.4, 25.3, 23.4, 21.4, 21.3, 14.5 |
| Mass (m/z) | 347.1 [M$^+$ + 1], 364.1 [M$^+$ + 18] |
| IR (KBr) | 3455, 2927, 1737.6, 1720.2, 1707.7, 1259, 1244 cm$^{-1}$ |
| m.p. | 156-158° C. |
| [α]$_D$ | 116 (c = 1 in CHCl$_3$) |

Example 4

(Z)-3β-Hydroxy-5β-preg-17(20)-ene-11-one acetate (1.16)

Potassium tert-butoxide (159.28 mL, 159.2 mmol, 1M solution in THF) is added to a solution of ethyltriphenylphosphonium bromide (61.16 g, 164.8 mmol) in THF (150 mL) is added drop wise over 1 h under an inert atmosphere at −5° C. The resulting dark pink colored reaction mixture is warmed to 10-15° C. and stirred for an additional 1 h at the same temperature. A solution of Compound 55 (19.0 g, 54.9 mmol) in THF (50 mL) is introduced slowly to the above Wittig ylide suspension at −5° C. The solution is stirred for an additional 10-20 minutes and the reaction mixture is allowed to warm to ambient temperature slowly. Stirring is continued for about 3-4 h. Upon complete disappearance of starting material, as evidenced by TLC, the reaction mixture is quenched with saturated aqueous NH$_4$Cl solution (75 mL). The aqueous layer is extracted with EtOAc (2×150 mL) and the combined organic extracts are washed with saturated brine solution (100 mL) and dried over MgSO$_4$ (75 g). The solvent is removed under vacuum and the crude material is purified by column chromatography [49(W)×600(L) mm, 60-120 Mesh silica, 300 g] eluting with ethyl acetate/hexane (1:20) [25 mL fractions, 10 mL/min elution, monitored by TLC with p-anisaldehyde charring; R$_f$ for Compound 1.16=0.54 and R$_f$ for Compound 1.15=0.06 in EtOAc/Hexane (1:6)] to afford Compound 1.16 (15.5 g, 78.8% yield) as a thick colorless liquid, which solidified slowly after 1-2 days at 0° C. Table 5 describes the measured properties of the product.

TABLE 5

| | |
|---|---|
| $^1$H NMR (500 MHz, CDCl$_3$) | δ = 5.20-5.15 (m, 1H), 5.03 (s, 1H), 2.86 (d, J = 10.0 Hz, 1H), 2.60 (d, J = 10.0 Hz, 1H), 2.46-2.28 (m, 5H), 2.01 (s, 3H), 1.94-1.62 (m, 5H), 1.60-1.52 (m, 6H), 1.48-1.45 (m, 1H), 1.41-1.36 (m, 4H), 1.20 (s, 3H), 0.82 (s, 3H) |
| $^{13}$C NMR (125 MHz, CDCl$_3$) | δ = 210.9, 170.5, 147.2, 114.7, 70.0, 56.1, 55.6, 51.5, 47.4, 37.9, 35.9, 34.4, 31.6, 30.7, 29.8, 26.4, 25.9, 25.5, 24.0, 23.5, 21.3, 17.9, 12.8 |
| Mass (m/z) | 359.2 [M$^+$ + 1], 376.2 [M$^+$ + 18] |

TABLE 5-continued

| | |
|---|---|
| IR (CHCl$_3$) | 3421, 2928, 1734, 1704, 1377, 1243 cm$^{-1}$ |
| m.p. | 88.5-91.2° C. |
| [α]$_D$ | +30 (c = 1 in CHCl$_3$) |

Example 5

Methyl (E)-3β-hydroxy-5β-chola-16(17), 22(23)-diene-24-oate acetate (1.17)

Methyl propiolate (9.68 g, 114.95 mmol) is added to a solution of Compound 1.16 (16.5 g, 46 mmol) in CH$_2$Cl$_2$ (220 mL) 0° C. The reaction mixture is warmed to ambient temperature and stirred for 1 h under an inert atmosphere. Ethyl aluminum dichloride (17.5 g, 137.8 mmol) is introduced to the above mixture at 0° C. drop wise and the resulting reaction mass is again warmed to ambient temperature and stirred overnight. Upon completion of the reaction, as evidenced by TLC, the crude reaction mixture is quenched with ice-water (100 mL) and the aqueous layer is extracted with EtOAc (3×150 mL). The combined organic layer is washed with saturated brine solution (100 mL) and dried over MgSO$_4$ (50 g). The solvent is removed under vacuum and the crude material is purified by column chromatography [49(W)×600(L) mm, 60-120 Mesh silica, 300 g] eluting with ethyl acetate/hexane (1:7) [15 mL fractions, 10 mL/min elution, monitored by TLC and detected with either by UV light (254 nm) lamp or p-anisaldehyde charring; R$_f$ for Compound 1.17=0.36 and R$_f$ for Compound 1.16=0.54 in EtOAc/Hexane (1:6)] to afford Compound 1.17 (16 g, 79% yield) as a colorless semi solid. Table 6 describes the measured properties of the product.

TABLE 6

| | |
|---|---|
| $^1$H NMR (500 MHz, CDCl$_3$) | δ = 6.89 (dd, J = 8.0, 16 Hz, 1H), 5.81 (d, J = 15 Hz, 1H), 5.48 (s, 1H), 5.03 (s, 1H), 3.73 (s, 3H), 2.95 (t, J = 6.5 Hz, 1H), 2.45-2.36 (m, 2H), 2.30-2.17 (m, 2H), 2.04 (s, 3H), 2.00-1.79 (m, 5H), 1.58 (s, 3H), 1.49-1.18 (m, 9H), 1.16 (s, 3H), 0.70 (s, 3H) |
| $^{13}$C NMR (125 MHz, CDCl$_3$) | δ = 209.7, 170.1, 166.6, 154.4, 152.3, 124.5, 119.1, 69.7, 56.3, 53.8, 52.3, 51.1, 49.8, 37.9, 35.7, 35.0, 34.4, 30.5, 30.4, 29.6, 26.2, 25.6, 25.2, 23.3, 21.1, 19.2, 17.3 |
| Mass (m/z) | 443.0 [M$^+$ + 1], 460.1 [M$^+$ + 18] |
| IR (CHCl$_3$) | 3438, 2930, 1729, 1706, 1653, 1448, 1435, 1243, 1022 cm$^{-1}$ |
| [α]$_D$ | +59 (c = 1 in CHCl$_3$) |
| HPLC purity | 94.4%; ret. time = 28.86, (Zorbax SB, C18; 250 × 4.6 mm, 5u), ACN: 5 mM TEA pH-2.5 with HClO$_4$ (Gradient); absorbance at 205 nm |

Example 6

Methyl 3β-hydroxy-5β-cholan-11-one-24-oate acetate (1.18)

10% Pd/C (2.9 g, 20 wt %) is added to a solution of Compound 1.17 (14.5 g, 32.8 mmol) in EtOAc (150 mL). The resulting slurry is hydrogenated in a Parr apparatus (50 psi) for 12 h. Upon complete disappearance of starting material, as evidenced by TLC [R$_f$ for Compound 1.18=0.43 and R$_f$ for Compound 1.17=0.43 in EtOAc/Hexane (1:3); however only Compound 1.17 is UV active from the conjugated ester chromophore], the crude reaction mixture is filtered through a small plug of Celite and the solvent is removed under vacuum to afford Compound 1.18 (14 g, 95.7% yield) as a colorless solid. Table 7 describes the measured properties of the product.

TABLE 7

| $^1$H NMR (500 MHz, CDCl$_3$) | δ = 5.03 (s, 1H), 3.73 (s, 3H), 2.56 (d, J = 10 Hz, 1H), 2.38-2.19 (m, 5H), 2.04 (s, 3H), 1.86-1.13 (m, 20H), 1.12 (s, 3H), 0.86 (s, 3H), 0.62 (s, 3H) |
|---|---|
| $^{13}$C NMR (125 MHz, CDCl$_3$) | δ = 211.3, 174.3, 170.5, 70.0, 58.3, 55.7, 55.0, 51.4, 50.8, 46.8, 37.9, 36.7, 35.0, 34.3, 30.9, 30.7, 30.7, 29.7, 28.3, 26.6, 25.9, 25.5, 23.6, 23.5, 21.4, 17.9, 12.7 |
| Mass (m/z) | 447.1 [M$^+$ + 1], 464.1 [M$^+$ + 18] |
| IR (KBr) | 3449, 2927, 1734, 1704, 1381, 1262, 1243 cm$^{-1}$ |
| m.p. | 174.2-175.7° C. (From CH$_2$Cl$_2$/Hexane) (Observed); 174.8-176.2° C. (Reported) |
| [α]$_D$ | +39 (c = 1 in CHCl$_3$) |

Example 7

Methyl 3β-hydroxy-5β-chol-9(11)-ene-24-oate acetate (1.19)

PtO$_2$ (5.0 g, 100 wt %) is added to a solution of 1.18 (5.0 g, 11.2 mmol) in EtOAc (75 mL) in the presence of catalytic amount of AcOH (2.0 mL). The resulting slurry is hydrogenated in a Parr apparatus (70 psi) for about 14-16 h. Upon completion of the reaction, the crude mixture is filtered through a small plug of Celite and the solvent is removed under vacuum. The crude product is used for the elimination reaction without further purification.

SOCl$_2$ (1.98 g, 16.78 mmol) is introduced to a solution of the above crude material in pyridine (100 mL) drop wise at 0° C. The resulting reaction mixture is warmed to ambient temperature and stirred for about 1 h. Upon completion of the reaction, as evidenced by TLC, pyridine is removed under vacuum. The crude residue is diluted with ethyl acetate (100 mL) and washed with water (2×50 mL), saturated brine solution (100 mL) and dried over MgSO$_4$ (40 g). The solvent is evaporated under vacuum and the crude material is purified by column chromatography [49(W)×600(L) mm, 60-120 Mesh silica, 120 g] eluting with ethyl acetate/hexane (1:10) [10 mL fractions, 5 mL/min elution, monitored by TLC with p-anisaldehyde charring; R$_f$ for Compound 1.19=0.51 and R$_f$ for Compound 1.18=0.22 in EtOAc/Hexane (1:6)] to afford Compound 1.19 (4.1 g, 85.4% yield) as a colorless solid. Table 8 describes the measured properties of the product.

TABLE 8

| $^1$H NMR (500 MHz, CDCl$_3$) | δ = 5.33 (s, 1H), 5.03 (s, 1H), 3.66 (s, 3H), 2.37-2.32 (m, 1H), 2.46-2.21 (m, 1H), 2.11-2.04 (m, 1H), 2.03 (s, 3H), 1.99-1.10 (m, 22H), 1.07 (s, 3H), 0.92 (d, J = 7.0 Hz, 3H), 0.58 (s, 3H) |
|---|---|
| $^{13}$C NMR (125 MHz, CDCl$_3$) | δ = 174.6, 170.6, 140.1, 118.9, 71.2, 56.1, 53.3, 51.3, 42.0, 40.9, 38.9, 37.3, 36.4, 35.2, 31.9, 31.4, 31.0, 30.9, 30.1, 28.2, 26.9, 26.2, 26.1, 25.3, 21.4, 17.9, 11.6 |
| Mass (m/z) | 448.2 [M$^+$ + 18] |
| IR (KBr) | 3447, 2935, 1735, 1379, 1261, 1245 cm$^{-1}$ |
| m.p. | 188.6-191.2° C. (From CH$_2$Cl$_2$/Hexane) (Observed); 174-175° C. (Reported) |
| [α]$_D$ | +37 (c = 1 in CHCl$_3$) |

Example 8

Methyl 3β-hydroxy-5β-chol-9(11)-ene-12-one-24-oate acetate (1.20)

CrO$_3$ (8.0 g, 100 wt %, 80.0 mmol) is added to a solution of Compound 1.19 (8.0 g, 18.6 mmol) in AcOH (150 mL). The resulting reaction mixture is heated at 60° C. for about 24-36 h. Upon complete disappearance of the precursor, acetic acid is evaporated under vacuum, and the crude material is dissolved in diethyl ether (400 mL). The organic layer is washed with water (2×100 mL), saturated brine solution (100 mL) and dried over MgSO$_4$ (40 g). The solvent is removed under vacuum and the crude material is purified by column chromatography [49(W)×600(L) mm, 60-120 Mesh silica, 120 g] eluting with ethyl acetate/hexane (1:5) [10 mL fractions, 3 mL/min elution, monitored by TLC and detected with UV light (254 nm) lamp; R$_f$ for Compound 1.20=0.28 and R$_f$ for Compound 1.19=0.61 in EtOAc/Hexane (1:4)] to afford Compound 1.20 (5 g, 60.5% yield) as a colorless solid. Table 9 describes the measured properties of the product.

TABLE 9

| $^1$H NMR (500 MHz, CDCl$_3$) | δ = 5.72 (s, 1H), 5.04 (s, 1H), 3.66 (s, 3H), 2.41-2.27 (m, 3H), 2.03 (s, 3H), 1.94-1.58 (m, 9H), 1.48-1.30 (m, 11H), 1.21 (s, 3H), 1.02 (d, J = 6.5 Hz, 3H), 0.91 (s, 3H) |
|---|---|
| $^{13}$C NMR (500 MHz, CDCl$_3$) | δ = 205.1, 174.5, 170.4, 164.2, 123.1, 70.3, 53.4, 53.0, 51.3, 47.2, 40.2, 37.7, 37.3, 35.2, 32.1, 31.4, 31.0, 30.6, 30.2, 27.3, 26.5, 25.9, 25.6, 24.1, 21.3, 19.4, 10.6 |
| Mass (m/z) | 445.0 [M$^+$ + 1], 462.1 [M$^+$ + 18] |
| IR | 3447, 2927, 2361, 2339, 1736, 1678, 1367, 1250 cm$^{-1}$ |
| m.p. | 185.8-188.1° C. (From CH$_2$Cl$_2$/Hexane) |
| [α]$_D$ | +62 (c = 1 in CHCl$_3$) |
| HPLC purity | 94.1%; ret. time = 23.89 (Hypersil BDS C18, 250 × 4.6 mm, 5u, CH$_3$CN: 5 mM TEA, pH-2.5 with HClO$_4$ (Gradient); absorbance at 240 nm |

Example 9

Methyl 3β-hydroxy-5β-cholane-12-one-24-oate acetate (1.21)

10% Pd/C (30 mg, 10 wt %) is added to a solution of Compound 1.20 (300 mg, 0.675 mmol) in EtOAc (30 mL). The resulting slurry is hydrogenated in a Parr apparatus (50 psi) for about 16 h. Upon complete disappearance of starting material by TLC [R$_f$ for Compound 1.21=0.44 and R$_f$ for Compound 1.20=0.44 in EtOAc/Hexane (3:7); however only Compound 1.20 is UV active from its enone chromophore; additionally charring of Compound 1.20 is faint but Compound 1.21 is bright], the crude reaction mixture was filtered through a small plug of Celite and the solvent is removed under vacuum to afford Compound 1.21 (270 mg, 90% yield) as a colorless solid. Table 10 describes the measured properties of the product.

TABLE 10

| $^1$H NMR (500 MHz, CDCl$_3$) | δ = 5.04 (s, 1H), 3.64 (s, 3H), 2.52-2.47 (m, 1H), 2.38-2.25 (m, 3H), 2.23-2.03 (m, 2H), 2.02 (s, 3H), 1.99-1.71 (m, 8H), 1.49-1.11 (m, 12H), 1.05 (s, 3H), 1.01 (s, 3H), 0.85-0.84 (d, J = 7.0 Hz, 3H) |
|---|---|
| $^{13}$C NMR (125 MHz, CDCl$_3$) | δ = 214.7, 174.6, 170.5, 70.2, 58.7, 57.5, 51.4, 46.5, 43.7, 38.4, 36.9, 35.7, 35.6, 35.5, 31.3, 30.7, 30.5, 27.5, 26.4, 25.9, 24.8, 24.3, 23.2, 21.4, 18.6, 11.7 |
| Mass (m/z) | 447.0 [M$^+$ + 1], 464.0 [M$^+$ + 18] |
| IR (KBr) | 3447, 2935, 1735, 1704, 1260, 1241 cm$^{-1}$ |
| m.p. | 179.6-182.7° C. (From CH$_2$Cl$_2$/Hexane) |
| [α]$_D$ | +69 (c = 1 in CHCl$_3$) |

Example 10

Methyl 5β-chola-3,12-dione-24-oate (1.22)

NaOH (73 mg, 1.8 mmol) is added to a solution of Compound 2.1 (270 mg, 0.6 mmol) in MeOH (10 mL). The resulting reaction mixture is stirred for about 2 h at ambient temperature. Upon completion of the reaction, as evidenced by TLC, MeOH is removed under vacuum and the crude product is diluted with ethyl acetate (20 mL). The organic layer is washed with saturated brine solution (10 mL) and dried over $MgSO_4$ (5.0 g). The solvent is removed under vacuum and the crude material is used in the esterification reaction without purification.

$SOCl_2$ (0.1 mL, 1.35 mmol) is added drop-wise to a solution of the above crude material in MeOH (10 mL) 0° C. The resulting reaction mixture is stirred at ambient temperature for about 1 h. Upon completion of the reaction, MeOH is removed under vacuum. The crude reaction mixture is diluted with EtOAc (30 mL), and the organic layer is washed with water (3×10 mL), saturated brine solution (15 mL) and dried over $MgSO_4$ (5 g). The solvent is evaporated under vacuum and the crude product is used for the oxidation reaction without purification.

PCC (1.0 g, 4.6 mmol) is introduced in 3 equal portions to a solution of the obtained ester in $CH_2Cl_2$ (25 mL) over about 5 minutes. The resulting reaction mixture is stirred at ambient temperature for about 3-4 h. Upon completion of the reaction, as evidenced by TLC, the crude reaction mixture is filtered through a pad of Celite. The solvent is removed under vacuum and the crude material is purified by column chromatography [19(W)×400(L) mm, 60-120 Mesh silica, 45 g] eluting with ethyl acetate/hexane (1:6) [10 mL fractions, 5 mL/min elution, monitored by TLC with p-anisaldehyde charring; $R_f$ for Compound 1.22=0.57 and $R_f$ for Compound 1.21=0.71 in EtOAc/Hexane (2:3)] to afford Compound 1.22 (170 mg, 70.8% yield) as a colorless solid. Table 11 describes the measured properties of the product.

TABLE 11

| | |
|---|---|
| $^1$H NMR (500 MHz, $CDCl_3$) | δ = 3.66 (s, 3H), 2.64-2.57 (m, 2H), 2.55-2.19 (m, 4H), 2.17-2.02 (m, 3H), 1.99-1.21 (m, 17H), 1.11 (s, 3H), 1.05 (s, 3H), 0.86 (d, J = 10.0 Hz, 3H) |
| $^{13}$C NMR (125 MHz, $CDCl_3$) | δ = 213.9, 211.8, 174.5, 58.5, 57.5, 51.4, 46.5, 44.2, 43.7, 42.1, 38.3, 36.9, 36.8, 35.6, 35.4, 31.3, 30.5, 27.4, 26.6, 25.4, 24.3, 22.1, 18.5, 11.7 |
| Mass (m/z) | 403.1 [M$^+$ + 1], 420.2 [M$^+$ + 18] |
| IR (KBr) | 3457, 2925, 1737, 1708, 1216, 1176 cm$^{-1}$ |
| m.p. | 133.7-135.9° C. (From $CH_2Cl_2$/Hexane) (Obs); 136.5-137.5° C. (Rep) |
| $[α]_D$ | +79 (c = 1 in $CHCl_3$) |

Example 11

Methyl Deoxycholate (1.22-Ester)

LiAlH(O-$^t$Bu) (332 mg, 1.3 mmol) is introduced drop-wise to a solution of Compound 1.22 (150 mg, 0.37 mmol) in THF (10 mL) under an inert atmosphere at ambient temperature. After being stirred for about 4-5 hr, the reaction mixture is quenched with Aqueous HCl (2 mL, 1N) and the crude mixture is diluted with EtOAc (30 mL), washed with water (15 mL), saturated brine solution (10 mL) and dried over $MgSO_4$ (3 g). The solvent is removed under vacuum, and the crude mass is purified by column chromatography [29(W)×500(L) mm, 230-400 Mesh silica, 50 g] eluting with MeOH/$CH_2Cl_2$ (1:20) [5 mL fractions, 3 mL/min elution, monitored by TLC with p-anisaldehyde charring; $R_f$ for Compound 1.22-ester=0.42 and $R_f$ for Compound 1.22=0.85 in MeOH/$CH_2Cl_2$ (1:9)] to afford methyl deoxycholate (Compound 1.22-ester) (110 mg, 72.8% yield) as a colorless solid. Table 12 describes the measured properties of the product.

TABLE 12

| | |
|---|---|
| $^1$H NMR (500 MHz, $CDCl_3$) | δ = 3.97 (s, 1H), 3.65 (s, 3H), 3.63-3.59 (m, 1H), 2.39-2.33 (m, 1H), 2.25-2.19 (m, 1H), 1.88-0.97 (m, 24H), 0.95 (d, J = 6.0 Hz, 3H), 0.90 (s, 3H), 0.67 (s, 3H) |
| $^{13}$C NMR (125 MHz, $CDCl_3$) | δ = 174.7, 73.1, 71.7, 51.4, 48.2, 47.3, 46.5, 42.1, 36.4, 36.0, 35.2, 35.1, 34.1, 33.6, 31.1, 30.9, 30.4, 28.6, 27.4, 27.1, 26.1, 23.6, 23.1, 17.3, 12.7 |
| Mass (m/z) | 407.1 [M$^+$ + 1], 424.2 [M$^+$ + 18] |
| IR (KBr) | 3419, 2937, 2864, 1740, 1724, 1448, 1377, 1043 cm$^{-1}$ |
| m.p. | 58.0-60.0° C. (under re-crystallization) |
| $[α]_D$ | +36 (c = 1 in $CHCl_3$) |

Example 11

Deoxycholic Acid

A solution of LiOH (23 mg, 0.55 mmol) in $H_2O$ (2.0 mL) is added to a solution of 1.22-ester (110 mg, 0.27 mmol) in THF (4 mL). The resulting reaction mixture is stirred for about 2-3 h at ambient temperature. Upon disappearance of the ester by TLC [$R_f$ for Compound DCA=0.35 and $R_f$ for Compound 1.22-ester=0.42 in MeOH/$CH_2Cl_2$ (1:9)], the crude reaction mixture is diluted with ethyl acetate (10 mL) and triturated with saturated brine solution to obtain a clear separation of the organic layer. The organic layer was washed with saturated $NH_4Cl$ solution (10 mL), and dried over $MgSO_4$ (3.0 g). The solvent is removed under vacuum and any trace of water is removed by azetroping with toluene (3×5 mL) to afford deoxycholic acid (DCA) (100 mg, 94.3% yield) as a colorless solid. Table 13 describes the measured properties of the product.

TABLE 13

| | |
|---|---|
| $^1$H NMR (500 MHz, DMSO) | δ = 3.77 (s, 1H), 3.38-3.33 (m, 1H), 2.20-2.15 (m, 1H), 2.08-2.02 (m, 1H), 1.92-0.90 (m, 24H), 0.84-083 (d, J = 5.0 Hz, 3H), 0.77 (s, 3H), 0.53 (s, 3H) |
| $^{13}$C NMR (125 MHz, DMSO) | δ = 175.9, 71.0, 69.9, 47.4, 46.2, 45.9, 41.6, 36.3, 35.7, 35.1, 35.0, 33.8, 32.9, 31.2, 31.2, 30.2, 28.6, 27.2, 26.9, 26.1, 23.5, 23.0, 16.9, 12.4 |
| Mass (m/z) | 392 [M$^+$, not detected], 410.2 [M$^+$ + 18] |
| IR | 3445, 2931, 2867, 1694, 1636, 1043 cm$^{-1}$ |
| m.p. | 173.2-175.5° C. (From THF/$CH_2Cl_2$) (Observed); 174-176° C. (Reported, Alfa Aesar) and 171-174° C. (Reported, Aldrich) |
| $[α]_D$ | +50 [c = 1 in MeOH and $CHCl_3$ (1:1)]; +54° (c = 2 in ethanol) [Alfa Aesar] |

The yield of products for the exemplary processes described in Examples 1 through 11 are described in Table 14.

TABLE 14

| Overall Yield of Synthetic DCA Process | | | | |
|---|---|---|---|---|
| Compound | MP (° C.) (observed) | MP (° C.) Reported | % Yield | Notes |
| Hydrocortisone | | | | |
| 1.13 | 128.9-131.1 | 128.0-131.0 | 79.00 | Hydrogenation, side chain cleavage, and PCC oxidation |
| 1.14 | 176.6-180.5 | | Crude | K-Selectride ® reduction |
| 1.15 | 156.0-158.0 | | 66.40 | Acetylation |
| 1.16 | 88.5-91.2 | | 78.80 | Wittig |
| 1.17 | | | 79.00 | Ene |
| 1.18 | 174.2-175.7 | | 95.80 | Hydrogenation (Pd/C) |

TABLE 14-continued

Overall Yield of Synthetic DCA Process

| Compound | MP (° C.) (observed) | MP (° C.) Reported | % Yield | Notes |
|---|---|---|---|---|
| 1.19 | 188.6-191.2 | 174.0-175.0 | 85.40 | Thionyl chloride/pyridine dehydration (2-step yield) |
| 1.20 | 185.8-188.1 | | 60.50 | Chromium trioxide allylic oxidation |
| 1.21 | 179.6-182.7 | | 90.00 | Hydrogenation (Pd/C) |
| 1.22 | 133.7-135.9 | 136.5-137.5 | 70.80 | Hydrolysis, esterification, and oxidation |
| 1.22-ester | 58.0-60.0 | | 72.80 | LiAlH(O-$^t$Bu)$_3$ reduction |
| DCA | 173.2-175.5 | 174.0-176.0 | 94.33 | Hydrolysis of ester |
| | | | 7.00 | Overall yield |

Example 12

Comparison of Carbon Content of Synthetic DCA Versus Bovine DCA

Synthetic DCA (three samples, prepared according to the methods disclosed above or according to WO 2008/157635 Examples 12-24 which is incorporated herein by reference in its entirety) and DCA purchased from SIGMA (Sigma Aldrich PO Box 14508 St. Louis, Mo. 63178), PIERCE (Pierce Protein Research Products PO Box 117, Rockford Ill. 61105 USA), and NZP (New Zealand Pharmaceuticals Limited, PO Box 1869, Palmerston North 4440, New Zealand) were analyzed for their percent fossil carbon and ppt (parts per trillion) $^{14}$C carbon content. The percent fossil carbon provides a measure of the amount of carbon in the molecule originating from fossil fuel, which is expected to have very little $^{14}$C due to decay of this isotope. Intermediates used in the synthesis of DCA are derived from fossil fuels. Conversely, DCA synthesized from animals is expected to have approximately 1 ppt $^{14}$C and little to no fossil content. These expectations are borne out in the analyses as shown in Table 15. (Radiocarbon analyses were carried out according to the American Society for Testing Materials ASTM D6866 procedure (ASTM international, 100 Barr Harbon Drive, PO Box C700, West Conshohocken, Pa. 19428-2959).

TABLE 15

Comparison of carbon content of DCA isolated from bovines versus synthetic DCA

| DCA | Fossil Carbon | ppt C$^{14}$ |
|---|---|---|
| Bovine DCA (SIGMA) | 0% | 1 ppt |
| Bovine DCA (PIERCE) | 0% | 1 ppt |
| Bovine DCA (NZP) | 2% | 1 ppt |
| Synthetic DCA (sample 1) | 13% | 0.87 ppt |
| Synthetic DCA (sample 2) | 12% | 0.88 ppt |
| Synthetic DCA (sample 3) | 11% | 0.89 ppt |

Accordingly, in one embodiment provided is method for distinguishing synthetic DCA from naturally derived DCA based on their fossil-derived carbon content and/or $^{14}$C content. In one aspect, provided is synthetic DCA having greater than 4% fossil-derived carbon. In another aspect, provided is synthetic DCA having less than 1 ppt $^{14}$C or less than 0.9 ppt $^{14}$C.

What is claimed is:

1. An aqueous pharmaceutical formulation comprising about 0.1% w/v to about 2% w/v deoxycholate and at least one pharmaceutically acceptable excipient and/or carrier, wherein the deoxycholate has a $^{14}$C content of less than 1 ppt.

2. The formulation of claim 1, wherein the deoxycholate has a $^{14}$C content of less than 0.9 ppt.

3. The pharmaceutical formulation of claim 1, which is suitable for subcutaneous injection.

4. The pharmaceutical formulation of claim 1, wherein the deoxycholate has a $^{14}$C content of 0.87 ppt.

5. The pharmaceutical formulation of claim 1, wherein the deoxycholate has a $^{14}$C content of 0.88 ppt.

6. The pharmaceutical formulation of claim 1, wherein the deoxycholate has a $^{14}$C content of 0.89 ppt.

* * * * *